United States Patent
Nasu

(10) Patent No.: US 11,646,111 B2
(45) Date of Patent: May 9, 2023

(54) MEDICAL IMAGE PROCESSING APPARATUS, MEDICAL IMAGE PROCESSING METHOD AND MEDICAL IMAGE PROCESSING SYSTEM

(71) Applicant: Ziosoft, Inc., Tokyo (JP)

(72) Inventor: Yu Nasu, Tokyo (JP)

(73) Assignee: ZIOSOFT, INC., Tokyo (JP)

( * ) Notice: Subject to any disclaimer, the term of this patent is extended or adjusted under 35 U.S.C. 154(b) by 386 days.

(21) Appl. No.: 16/517,814

(22) Filed: Jul. 22, 2019

(65) Prior Publication Data
US 2020/0027546 A1 Jan. 23, 2020

(30) Foreign Application Priority Data

Jul. 23, 2018 (JP) .............................. JP2018-138000

(51) Int. Cl.
*G16H 30/40* (2018.01)
*G06T 7/00* (2017.01)
(Continued)

(52) U.S. Cl.
CPC ........... *G16H 30/40* (2018.01); *A61B 6/5211* (2013.01); *G06T 7/0012* (2013.01); *A61B 6/032* (2013.01);
(Continued)

(58) Field of Classification Search
CPC ............ G16H 30/40; A61B 6/52–5294; A61B 6/02–037; A61B 8/145; A61B 8/483;
(Continued)

(56) References Cited

U.S. PATENT DOCUMENTS

2008/0317318 A1 12/2008 Scheuering et al.
2013/0307845 A1 11/2013 Kashima
(Continued)

FOREIGN PATENT DOCUMENTS

JP 2005-080989 A 3/2005
JP 2010-279425 A 12/2010
(Continued)

OTHER PUBLICATIONS

Japanese Office Action dated Apr. 19, 2022 issued in Japan Patent Application No. 2018-138000.

*Primary Examiner* — Vu Le
*Assistant Examiner* — Julius Chai
(74) *Attorney, Agent, or Firm* — Pearne & Gordon LLP

(57) ABSTRACT

A medical image processing apparatus includes an acquisition unit and a processing unit. The acquisition unit acquires volume data of a subject. The processing unit displays a three-dimensional image by rendering the acquired volume data, on a display unit. The processing unit displays a first object showing (i) a point on a body surface of the subject and (ii) a direction to the volume data in the three-dimensional image, and displays a two-dimensional image of a surface including the point on the body surface and being defined based on the direction, in the volume data. The processing unit acquires information of a first operation to change display of the two-dimensional image, and moves the point on the body surface along the body surface of the subject based on the first operation to update display of the first object and the two-dimensional image.

11 Claims, 22 Drawing Sheets

(51) Int. Cl.
  *A61B 6/00* (2006.01)
  *A61B 6/03* (2006.01)
(52) U.S. Cl.
  CPC ............... *G06T 2207/10081* (2013.01); *G06T 2207/30004* (2013.01)
(58) Field of Classification Search
  CPC ......... G06T 7/0012–0014; G06T 2207/10081; G06T 2207/30004
  See application file for complete search history.

(56) References Cited

U.S. PATENT DOCUMENTS

| | | |
|---|---|---|
| 2014/0187919 A1 | 7/2014 | Parthasarathy et al. |
| 2016/0174935 A1 | 6/2016 | Kashima |
| 2019/0272667 A1* | 9/2019 | Roundhill ............... G06T 19/00 |

FOREIGN PATENT DOCUMENTS

| | | |
|---|---|---|
| JP | 2013-240374 A | 12/2013 |
| WO | 2017-212063 A1 | 12/2017 |

* cited by examiner

MEDICAL IMAGE PROCESSING APPARATUS, MEDICAL IMAGE PROCESSING METHOD AND MEDICAL IMAGE PROCESSING SYSTEM

CROSS-REFERENCE TO RELATED APPLICATIONS

This application claims priority based on Japanese Patent Application No. 2018-138000, filed on Jul. 23, 2018, the entire contents of which are incorporated by reference herein.

TECHNICAL FIELD

The present disclosure relates to a medical image processing apparatus, a medical image processing method and a medical image processing system.

BACKGROUND ART

In recent years, there is a technique to generate an image based on volume data obtained by a computed tomography (CT) device with information obtained by an ultrasound probe in a real space. For example, in US 2014/0187919 discloses to acquire positional coordinates of an ultrasound probe in a real space and to generate a multi planer reconstruction (MPR) image corresponding to the acquired positional coordinates (see US 2014/0187919).

In recent years, a technique for virtually generating an image obtained using an ultrasound probe has become common.

SUMMARY OF INVENTION

In some cases, diagnosis and operation plans are made using CT data, and an operation is performed in accordance with pre-operative planning using an ultrasound image in an actual operation. The technique disclosed in US 2014/0187919 is applied to generation of a virtual ultrasound image, so that it is possible to acquire positional coordinates of an ultrasound probe in a virtual space and generate an MPR image corresponding to the acquired positional coordinates during the operation. Here, pre-operative planning may include a place to be touched by the ultrasound probe before an operation. When a doctor makes diagnosis, it is easier to understand accurate position of disease or the like in a subject when the subject is observed using a two-dimensional image than when the subject is observed using a three-dimensional image. A three-dimensional image is useful when the entire subject is observed from above. Therefore, for example, in a case where a user operates a two-dimensional image to update display while remembering an ultrasound image, it is preferable to ascertain to which position and which direction the changed two-dimensional image corresponds in a three-dimensional image.

The present disclosure is contrived in view of the above-described circumstances and provides a medical image processing apparatus, a medical image processing method and a medical image processing system which are capable of ascertaining to which position and which direction a changed two-dimensional image corresponds in a three-dimensional image in a case where a user operates the two-dimensional image to update display thereof.

According to one aspect of the disclosure, a medical image processing apparatus includes an acquisition unit and a processing unit. The acquisition unit acquires volume data of a subject. The processing unit displays a three-dimensional image by rendering the acquired volume data, on a display unit. The processing unit displays a first object showing (i) a point on a body surface of the subject and (ii) a direction with respect to the volume data in the three-dimensional image, on the display unit. The processing unit displays a two-dimensional image of a surface on the display unit. The surface includes the point on the body surface and is defined based on the direction, in the volume data. The processing unit acquires information of a first operation to change display of the two-dimensional image. The processing unit moves the point on the body surface along the body surface of the subject based on the first operation to update display of the first object and the two-dimensional image.

DESCRIPTION OF EMBODIMENTS

Hereinafter, an embodiment of the present disclosure will be described with reference to the accompanying drawings.

In the present disclosure, a medical image processing apparatus includes an acquisition unit, a processing unit and a display unit. The acquisition unit acquires volume data of a subject. The processing unit: displays a three-dimensional image by rendering the acquired volume data, on the display unit; displays a first object showing (i) a point on a body surface of the subject and (ii) a direction with respect to the acquired volume data in the three-dimensional image, on the display unit; displays a two-dimensional image of a surface on the display unit, the surface including a point on the body surface and being defined based on the direction, in the volume data; acquires information of a first operation to change display of the two-dimensional image; and moves the point on the body surface along the body surface of the subject based on the first operation to update display of the first object and the two-dimensional image.

According to the present disclosure, a user observes the subject using the two-dimensional image and easily understands an accurate position of disease or the like in the subject. The user can observe the entire subject from above by using the three-dimensional image. In this case, the user can ascertain to which position and which direction the two-dimensional image corresponds in the three-dimensional image.

First Embodiment

Figure 1:
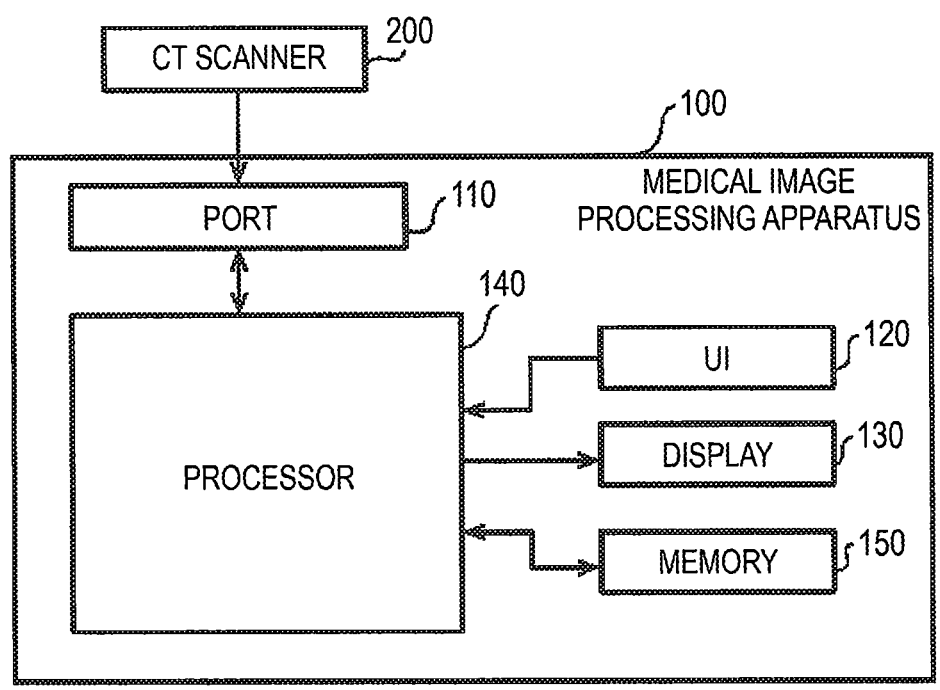
FIG. 1 is a block diagram showing a hardware configuration example of a medical image processing apparatus in a first embodiment.

FIG. 1 is a block diagram showing a configuration example of a medical image processing apparatus 100 in a first embodiment. The medical image processing apparatus 100 includes a port 110, a user interface (UI) 120, a display 130, a processor 140, and a memory 150.

A computed tomography (CT) scanner 200 is connected to the medical image processing apparatus 100. The medical image processing apparatus 100 acquires volume data from the CT scanner 200 and processes the acquired volume data. The medical image processing apparatus 100 may include a personal computer (PC) and software mounted on the PC.

The CT scanner 200 irradiates an internal organism with X-rays to obtain an image (CT image) using a difference in the absorption of X-rays due to tissues in the body. Examples of the internal organism include a human body and the like. The internal organism is an example of a subject.

A plurality of CT images may be obtained in time series. The CT scanner 200 generates volume data including information on any portion inside the internal organism. Any portion inside the internal organism may include various internal organs (for example, a brain, a heart, a kidney, a large intestine, a small intestine, a lung, a breast, mammary glands, and prostate glands). By acquiring the CT image, voxel values (CT values) of voxels in the CT image are obtained. The CT scanner 200 transmits volume data as the CT image to the medical image processing apparatus 100 via a wired circuit or a wireless circuit.

The CT scanner 200 includes a gantry (not shown) and a console (not shown). The gantry includes an X-ray generator (not shown) and an X-ray detector (not shown), and performs imaging at a predetermined timing indicated by the console to detect X-rays having passed through a human body and obtain X-ray detection data. The X-ray generator includes an X-ray tube (not shown). The console is connected to the medical image processing apparatus 100. The console acquires a plurality of pieces of X-ray detection data from the gantry and generates volume data based on the X-ray detection data. The console transmits the generated volume data to the medical image processing apparatus 100. The console may include an operation unit (not shown) for inputting patient information, imaging conditions related to CT imaging, contrast conditions related to administration of a contrast medium, and other information. The operation unit may include an input device such as a keyboard or a mouse.

The CT scanner 200 can also acquire a plurality of pieces of three-dimensional volume data by continuously performing image to generate a moving image. Data regarding a moving image based on a plurality of pieces of three-dimensional volume data is also referred to as four-dimensional (4D) data.

The CT scanner 200 may obtain CT images at a plurality of timings. The CT scanner 200 may obtain a CT image in a state where a subject is imaged. The CT scanner 200 may obtain a CT image in a state where a subject is not imaged.

The port 110 within the medical image processing apparatus 100 includes a communication port and an external device connection port and acquires volume data obtained from a CT image. The acquired volume data may be immediately transmitted to the processor 140 to be subjected to various processing, or may be stored in the memory 150 and then transmitted to the processor 140 to be subjected to various processing. In addition, the volume data may be acquired through a recording medium or recording media.

The volume data imaged by the CT scanner 200 may be transmitted from the CT scanner 200 to an image data server (picture archiving and communication systems: PACS) (not shown) and stored therein. The port 110 may acquire the volume data from the image data server instead of acquiring the volume data from the CT scanner 200. In this manner, the port 110 functions as an acquisition unit that acquires various data such as volume data.

The UI 120 may include a touch panel, a pointing device, a keyboard, or a microphone. The UI 120 receives any input operation from a user of the medical image processing apparatus 100. The user may include a doctor, a radiology technician, or other paramedic staffs.

The UI 120 receives operations such as designation of a region of interest (ROI) and setting of luminance conditions in the volume data. The region of interest may include regions of various tissues (for example, blood vessels, a bronchus, an internal organ, a bone, a brain, a heart, a foot, a neck, and a blood flow). The tissues may broadly include tissues of an internal organism such as lesion tissues, normal tissues, internal organs, and organs. In addition, the UI 120 may receive operations such as designation of a region of interest and setting of luminance conditions in volume data or an image based on the volume data (for example, a three-dimensional image and a two-dimensional image to be described later).

The display 130 may include a liquid crystal display (LCD) and displays various pieces of information. The various pieces of information may include a three-dimensional image and a two-dimensional image obtained from volume data. The three-dimensional image may include a volume rendering image, a surface rendering image, a virtual endoscope image (VE image), a virtual ultrasound image, a curved planar reconstruction (CPR) image, and the like. The volume rendering image may include a ray-sum image (also referred to simply as a "SUM image"), a maximum intensity projection (MIP) image, a minimum intensity projection (MinIP) image, an average value (average) image, or a ray-cast image. The two-dimensional image may include an axial image, a sagittal image, a coronal image, a multi planer reconstruction (MPR) image, and the like. The three-dimensional image and the two-dimensional image may include a color fusion image.

The memory 150 includes various primary storage devices such as a read only memory (ROM) and a random access memory (RAM). The memory 150 may include a secondary storage device such as a hard disk drive (HDD) and a solid state drive (SSD). The memory 150 may include a tertiary storage device such as a USB memory or an SD card. The memory 150 stores various pieces of information and programs. The various pieces of information may include volume data acquired by the port 110, an image generated by the processor 140, setting information set by the processor 140, and various programs. The memory 150 is an example of a non-transitory recording medium in which programs are recorded.

The processor 140 may include a central processing unit (CPU), a digital signal processor (DSP), or a graphics processing unit (GPU). The processor 140 functions as a processing unit 160 performing various processes and control by executing a medical image processing program stored in the memory 150.

Figure 2:
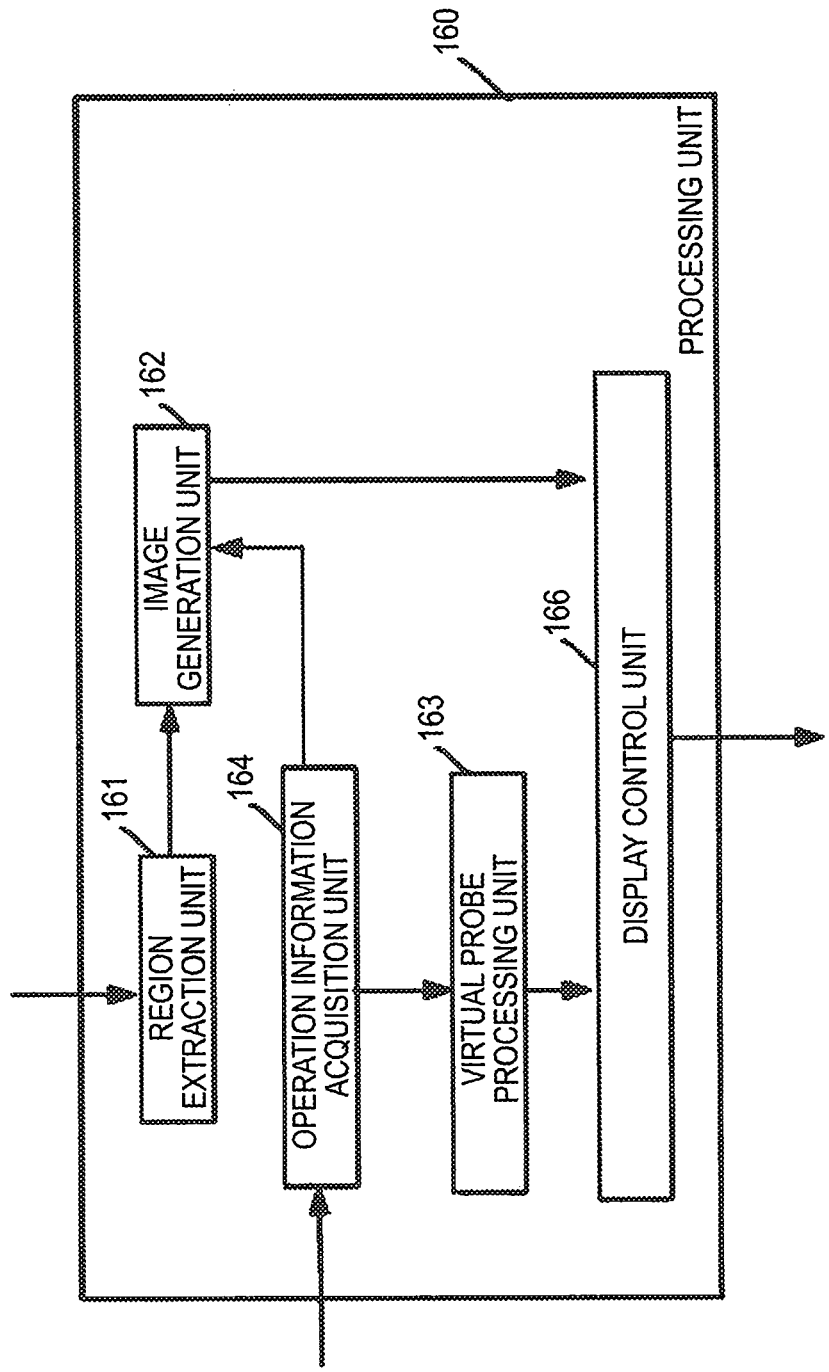
FIG. 2 is a block diagram showing a functional configuration example of the medical image processing apparatus.

FIG. 2 is a block diagram showing a functional configuration example of the processing unit 160.

The processing unit 160 includes a region extraction unit 161, an image generation unit 162, a virtual probe processing unit 163, an operation information acquisition unit 164, and a display control unit 166.

The processing unit 160 controls units of the medical image processing apparatus 100. The units included in the processing unit 160 may work as different functions by one piece of hardware or may be realized as different functions by a plurality of pieces of hardware. In addition, the units included in the processing unit 160 may work by dedicated hardware parts.

The region extraction unit 161 may perform segmentation processing in volume data. In this case, the UI 120 receives an instruction from a user, and the instructed information is transmitted to the region extraction unit 161. The region extraction unit 161 may perform segmentation processing from the volume data by a general method based on the instructed information and may extract (segment) a region of interest. In addition, a region of interest may be set manually by a user's detailed instruction. Further, in a case where an object to be observed is determined in advance, the region extraction unit 161 may perform segmentation processing from the volume data without a user's instruction or may extract a region of interest including an object to be observed. The region to be extracted may include regions of various tissues (for example, blood vessels, a bronchus, an internal organ, a bone, a brain, a heart, a foot, a neck, a blood flow, mammary glands, a breast, and a tumor).

The region extraction unit 161 may extract a body trunk of a subject ps as a region of interest. The region extraction unit 161 may extract the body trunk of the subject ps in accordance with, for example, region growing. The body trunk may correspond to, for example, a trunk portion of the subject ps or may be a portion including a breast and an abdomen. The body trunk may include areas related to the body trunk of the subject ps such as a head portion, a trunk portion, an arm portion, and a foot portion.

The image generation unit 162 may generate a three-dimensional image or a two-dimensional image based on volume data acquired by the port 110. The image generation unit 162 may generate a three-dimensional image (for example, a raycast image) or a two-dimensional image (for example, an MPR image) from the volume data acquired by the port 110 based on a designated region or a region extracted by the region extraction unit 161.

The virtual probe processing unit 163 generates a virtual probe pr as a UI object which shows an ultrasound probe used in a real space. The virtual probe pr may include a 3D virtual probe pr1 displayed together with a three-dimensional image. The 3D virtual probe pr1 may be displayed so as to be superimposed on the three-dimensional image. The 3D virtual probe pr1 comes into contact with the subject ps represented by a three-dimensional image in the three-dimensional image in a virtual space and is movable on a body surface of the subject ps. The 3D virtual probe pr1 may be moved along the body surface of the subject ps.

The virtual probe pr may include a 2D virtual probe pr2 displayed together with a two-dimensional image. The 2D virtual probe pr2 may be displayed so as to be superimposed on the two-dimensional image. The 3D virtual probe pr1 displayed together with the three-dimensional image corresponds to the 2D virtual probe pr2 displayed together with the two-dimensional image. That is, the position and direction of the 3D virtual probe pr1 on the three-dimensional space match and correspond to the position and direction of the 2D virtual probe pr2 in a two-dimensional plane.

Therefore, in a case where the position and direction of the 3D virtual probe pr1 in the three-dimensional space change, the position and direction of the 2D virtual probe pr2 in a two-dimensional plane may change. In contrast, in a case where the position and direction of the 2D virtual probe pr2 in the two-dimensional plane change, the position and direction of the 3D virtual probe pr1 in the three-dimensional space may change. The virtual probe processing unit 163 determines the position and direction of the 3D virtual probe pr1 so that the 3D virtual probe pr1 displayed together with the three-dimensional image maintains a contact with the body surface of the subject ps represented by the three-dimensional image even when a display range of the two-dimensional image in the two-dimensional plane changes.

The operation information acquisition unit 164 acquires information of various operations on a two-dimensional image through the UI 120.

The various operations may include an operation (also referred to as a slice paging operation) to move a two-dimensional image showing any cross-section (also referred to as, for example, an MPR surface SF or a slice) in volume data. The slice paging operation may be an operation to change the MPR surface SF to another MPR surface SF parallel to the MPR surface SF. The operation information acquisition unit 164 may detect the acquisition of slice paging for an MPR image G1 by a slider GUI (not shown) as an example of the UI 120 detecting, for example, a slide in a vertical direction.

The various operations may include an operation to move a two-dimensional image in any cross-section (within a cross-section) in volume data (also referred to as a panning operation). That is, the panning operation may be an operation to move a display range of the MPR surface SF in parallel in the MPR image G1 of the MPR surface SF. The operation information acquisition unit 164 may acquire a panning operation on the MPR image G1 by the UI 120 detecting a dragging operation on the MPR image G1 displayed on the display 130.

The various operations may include an operation to rotate any image in any cross-section in volume data (also referred to as a rotation operation). That is, the rotation operation may be an operation to rotate the MPR image G1 without changing the MPR surface SF of the MPR image G1. The operation information acquisition unit 164 may acquire a rotation operation by the UI 120 detecting a dragging operation for rotation with respect to a rotation instructing unit rp (see FIG. 4B) of the 2D virtual probe pr2 displayed on the display 130.

The image generation unit 162 may generate a three-dimensional image or a two-dimensional image based on operation information acquired by the operation information acquisition unit 164. The virtual probe processing unit 163 may generate the virtual probe pr (the 3D virtual probe pr1 and the 2D virtual probe pr2) based on operation information acquired by the operation information acquisition unit 164.

The display control unit 166 displays various data, information, and images on the display 130. The display control unit 166 may display the three-dimensional image or the two-dimensional image generated by the image generation unit 162. The display control unit 166 may display the virtual probe pr generated by the virtual probe processing unit 163. In this case, the display control unit 166 may display the 3D virtual probe pr1 so as to be superimposed on the three-dimensional image. The display control unit 166 may display the 2D virtual probe pr2 so as to be superimposed on the two-dimensional image.

In this manner, the display control unit 166 may visualize as a three-dimensional image or a two-dimensional image based on volume data acquired from the CT device 200. The display control unit 166 may visualized show the 3D virtual probe pr1 and the 2D virtual probe pr2 so as to indicate a positional relationship between the three-dimensional image and the two-dimensional image.

In the present embodiment, a raycast image is mainly exemplified as a three-dimensional image G2, but another three-dimensional image may be used. The MPR image G1 is mainly exemplified as a two-dimensional image, but another two-dimensional image may be used.

The three-dimensional image G2 may include a three-dimensional image G2A on which the 3D virtual probe pr1 moving during a slice paging operation is superimposed, a three-dimensional image G2B on which the 3D virtual probe pr1 moving during a panning operation is superimposed, and a three-dimensional image G2C on which the 3D virtual probe pr1 rotating during a rotation operation is superimposed. The MPR image G1 may include an MPR image G1A obtained during a slice paging operation, an MPR image G1B obtained during a panning operation, and an MPR image G1C obtained during a rotation operation.

Next, an example of movement of the 3D virtual probe pr1 on the three-dimensional image G2 will be described.

Figure 3A:
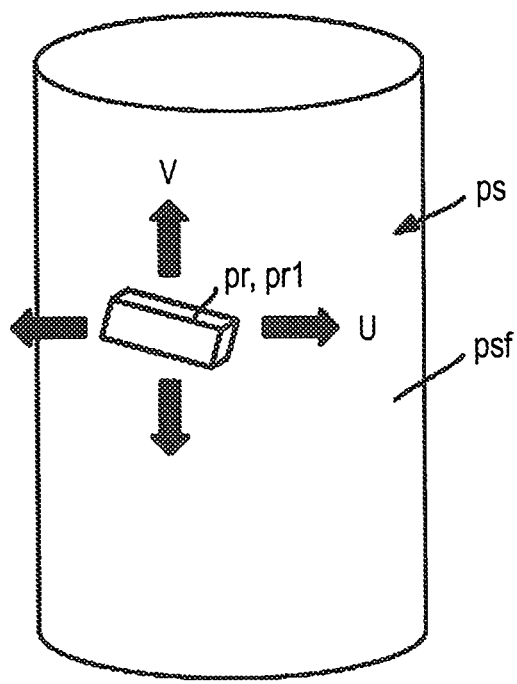
FIG. 3A is a diagram showing an example of movement of a virtual probe on a body surface of a subject shown by a three-dimensional image.
Figure 3B:
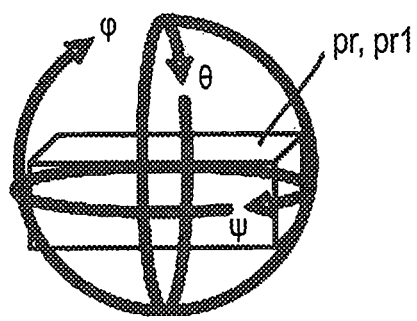
FIG. 3B is a diagram showing an example of rotation of a virtual probe on a body surface of a subject shown by a three-dimensional image.

FIG. 3A is a diagram showing an example of movement of the 3D virtual probe pr1 on a body surface psf of the subject ps shown by the three-dimensional image G2. FIG. 3B is a diagram showing an example of movement of the 3D virtual probe pr1 on the body surface psf of the subject ps shown by the three-dimensional image G2. In FIG. 3B, the body surface psf of the subject ps is not shown.

The 3D virtual probe pr1 may move on the body surface psf in accordance with an operation on the MPR image G1 through the UI 120. The 3D virtual probe pr1 may move on the body surface psf in accordance with an operation on the three-dimensional image G2 through the UI 120.

The virtual probe pf1 may move along the body surface psf of the subject ps. The virtual probe pf1 may be rotated on the body surface psf of the subject ps. Therefore, the virtual probe pf1 is not separated from the body surface psf, and at least one point of the virtual probe may be brought into contact with the body surface psf or the virtual probe may be brought into contact with the body surface psf in a surface contact manner. The virtual probe pf1 can be moved or rotated while maintaining a contact with the body surface psf.

As shown in FIG. 3A, the 3D virtual probe pr1 is movable on the body surface psf with two degrees of freedom in u and v directions. As shown in FIG. 3B, the 3D virtual probe pr1 is rotatable on the body surface psf with three degrees of freedom in a θ direction, a φ direction, and a Ψ direction.

A rotation direction of the 3D virtual probe pr1 received in the three-dimensional image G2 is may limit to any two directions or one direction (for example, the Ψ direction) among the above-described three directions. Since the degree of freedom of the 3D virtual probe pr1 in the rotation direction is limited, it becomes easy for a user operating the 3D virtual probe pr1 to intuitively know rotation through the operation, whereby operability is improved.

Figure 4A:
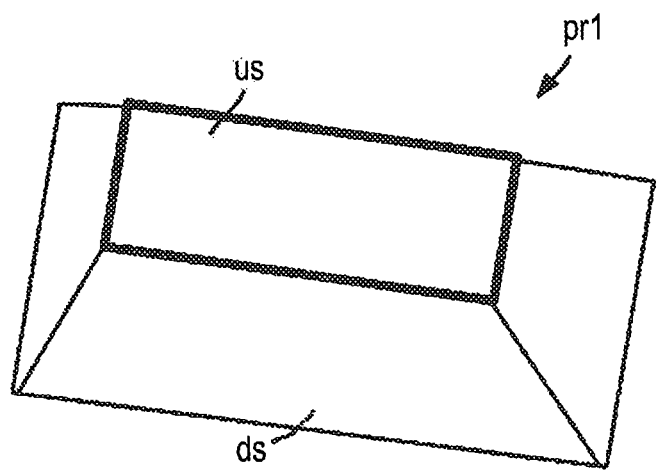
FIG. 4A is a diagram showing an example of a 3D virtual probe.
Figure 4B:
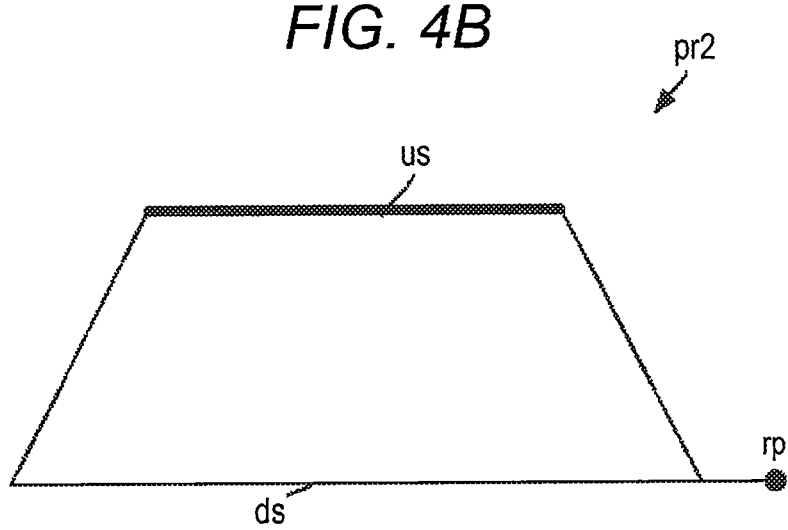
FIG. 4B is a diagram showing an example of a 2D virtual probe.

FIGS. 4A and 4B are diagrams showing an example of the virtual probe pr (the 3D virtual probe pr1 and the 2D virtual probe pr2). The 3D virtual probe pr1 shown in FIG. 4A is displayed together with a three-dimensional image. The 2D virtual probe pr2 shown in FIG. 4B is displayed together with the MPR image G1.

Although the 3D virtual probe pr1 and the 2D virtual probe pr2 may be the same three-dimensional UI object, the virtual probes are obliquely viewed in FIG. 4A and viewed in a side view in FIG. 4B, and thus the virtual probes are viewed differently between FIGS. 4A and 4B. The virtual probe pr has an upper surface us and a lower surface ds, and it is assumed that ultrasound waves are virtually transmitted along a direction from the upper surface us to the lower surface ds. That is, it is assumed that the virtual probe pr emits virtual ultrasound waves. Since the lower surface ds of the virtual probe pr comes into contact with the body surface psf of the subject ps, virtual ultrasound waves are transmitted from the lower surface ds to the inside of the body of the subject ps (the inner side of the body surface psf illustrated in a cylindrical shape). A passage through which the virtual ultrasound waves pass may be represented by a one-dimensional straight line or a region in a two-dimensional plane (parallel to a straight line) including the straight line. This two-dimensional plane is an MPR surface SF.

Figure 5:
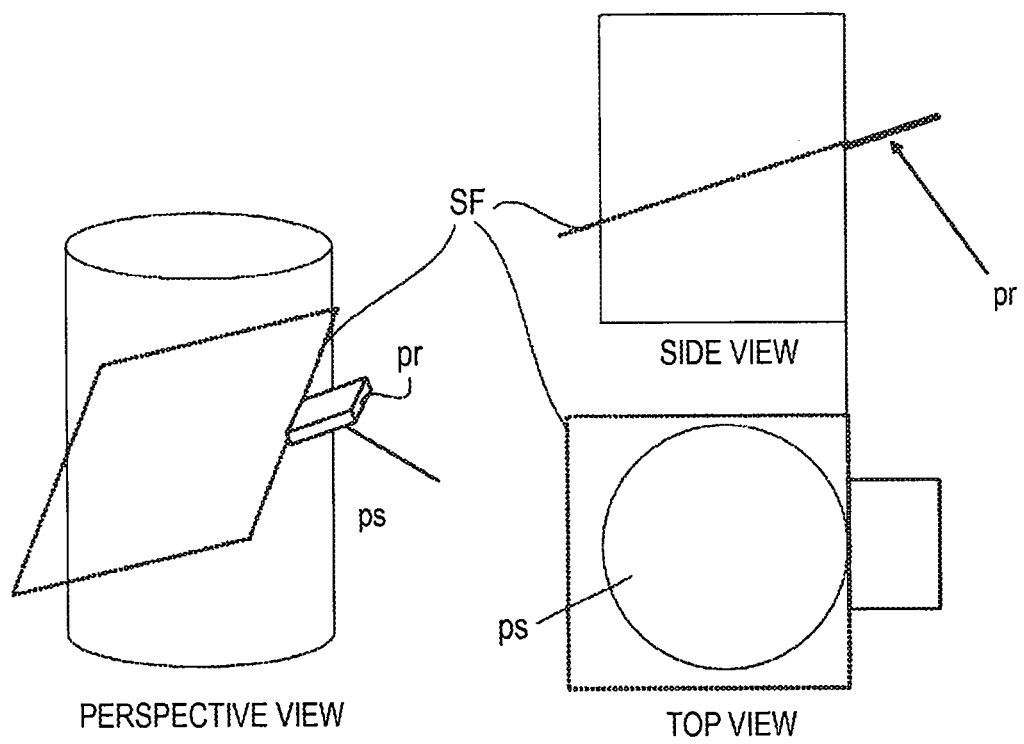
FIG. 5 is a diagram showing an example of a positional relationship between a subject, a virtual probe, and an MPR surface in a three-dimensional space.

FIG. 5 is a diagram showing an example of a positional relationship between the subject ps, the virtual probe pr, and the MPR surface SF in a three-dimensional space.

In FIG. 5, the subject ps is illustrated as a cylinder and the virtual probe pr is illustrated as a plate. In FIG. 5, it is assumed that virtual ultrasound waves transmitted from the virtual probe pr move inside the body of the subject ps along an extension line of a plate illustrating the 3D virtual probe pr1. In this case, this extension line is a path of the virtual ultrasound waves and along with the MPR surface SF. The appearance on the MPR surface SF is shown as an MPR image. That is, the MPR image is equivalent to a virtual ultrasound image.

Figure 6:
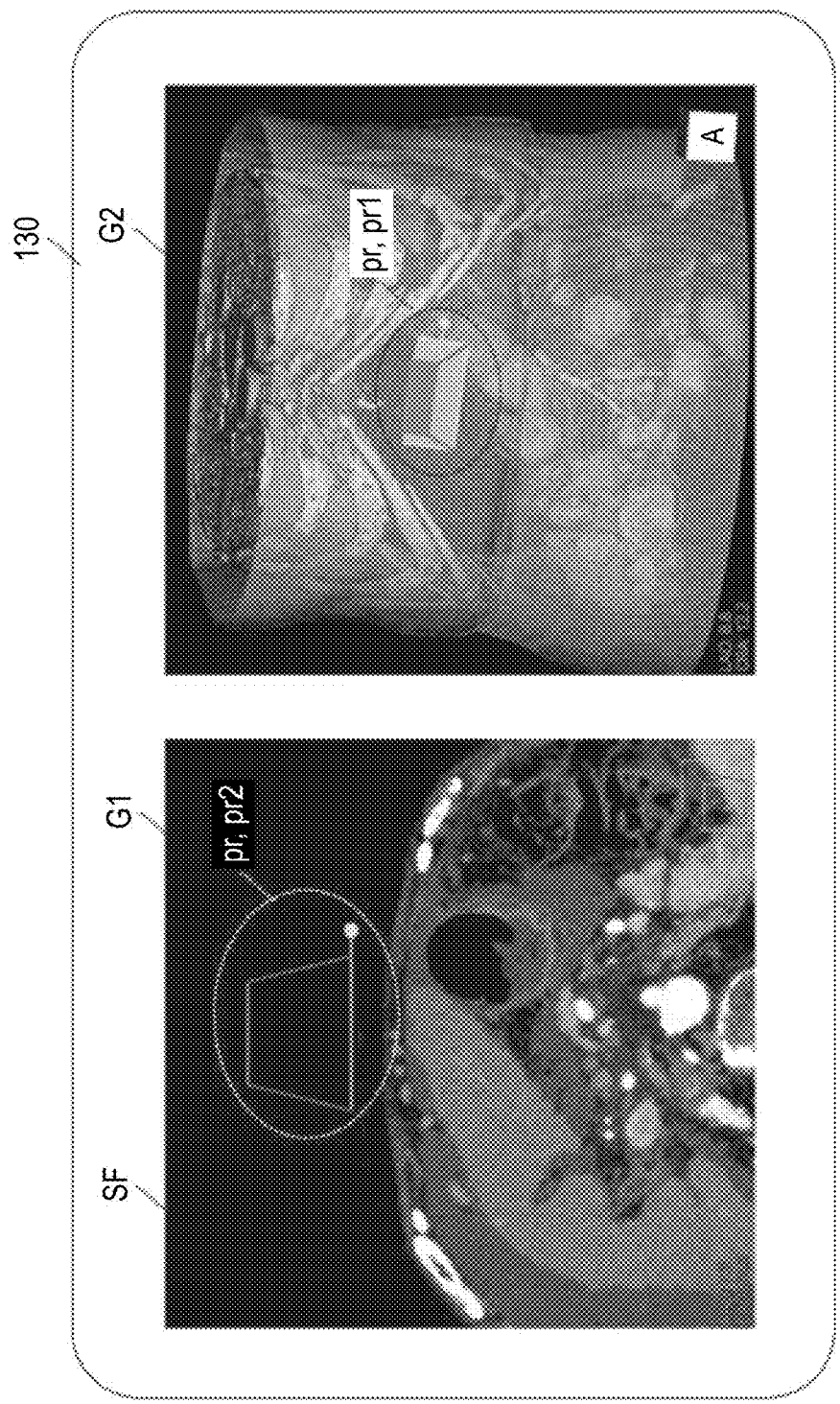
FIG. 6 is a diagram showing a display example using a display.

FIG. 6 is a diagram showing a display example using the display 130.

The display 130 displays a set including the three-dimensional image G2 and the 3D virtual probe pr1 and a set including the MPR image G1 and the 2D virtual probe pr2. The display 130 may simultaneously display the three-dimensional image G2, the 3D virtual probe pr1, the MPR image G1, and the 2D virtual probe pr2. Thereby, the user can easily ascertain details of the MPR image G1 and the three-dimensional image G2 and ascertain which position and direction of the subject ps in the three-dimensional image G2 correspond to the MPR image G1. Accordingly, for example, the user can recognize which organ of the subject ps is seen in the MPR image G1 generated based on the virtual probe pr, by bringing the virtual probe pr into contact with a certain position of the subject ps in a certain direction.

The display 130 may display the set including the three-dimensional image G2 and the 3D virtual probe pr1 and the set including the MPR image G1 and the 2D virtual probe pr2 at different timings. The display 130 may not display the 2D virtual probe pr2 corresponding to the MPR image G1.

Figure 7:
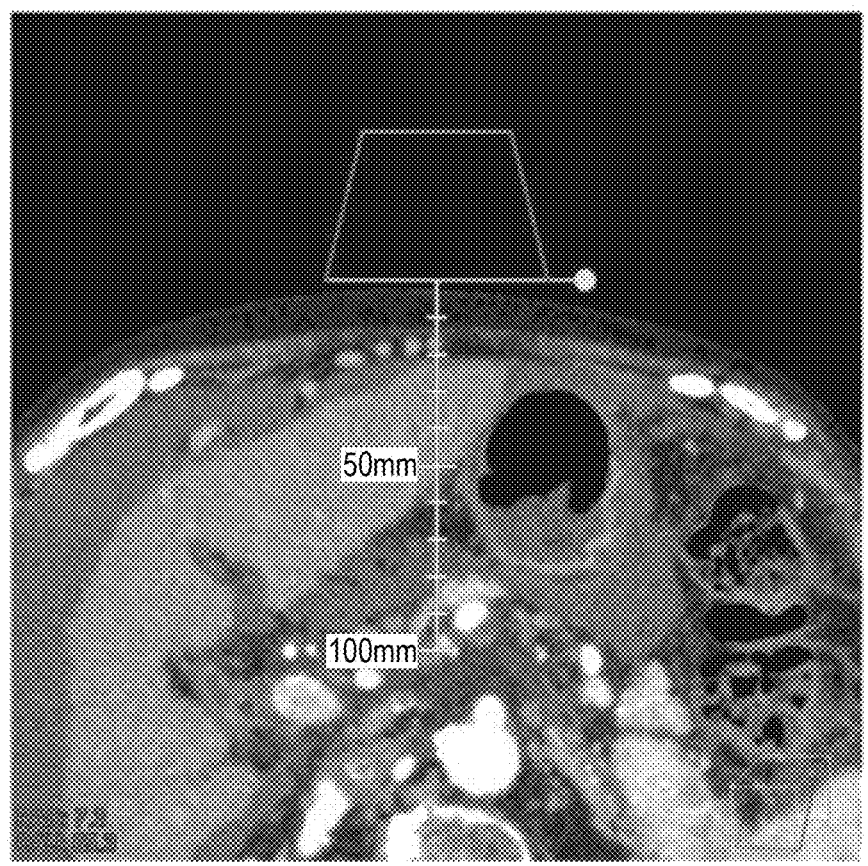
FIG. 7 is a diagram showing an example in which a scale display is superimposed on an MPR image.

FIG. 7 is a diagram showing an example in which a scale display is superimposed on the MPR image G1.

In FIG. 7, a distance from the body surface psf of the subject ps coming into contact with the 2D virtual probe pr2 is displayed in an overlapping manner. Here, as an example, a range from 0 mm to 100 mm is shown as information of the distance. In this manner, the medical image processing apparatus 100 superimposes a scale display on the MPR image G1, so that the user can easily confirm, for example, a distance to an affected area of an observation target in the subject ps. The user can easily confirm whether or not there is an importance organ or blood vessel on a straight line on which virtual ultrasound waves transmitted from the 2D virtual probe pr2 move. The medical image processing apparatus 100 can run a simulation of puncture while confirming a scale display, and it is possible to improve safety in puncture. Treatment of the puncture may include burning of the affected area. A scale may be displayed obliquely from the side of the 2D virtual probe pr2, assuming a case of an endoscopic ultrasound aspiration needle. In this manner, the medical image processing apparatus 100 may make pre-operative planning by performing a scale display on the MPR image G1.

Next, operations of the medical image processing apparatus 100 according to an operation on the MPR image G1 will be described.

Figure 8:
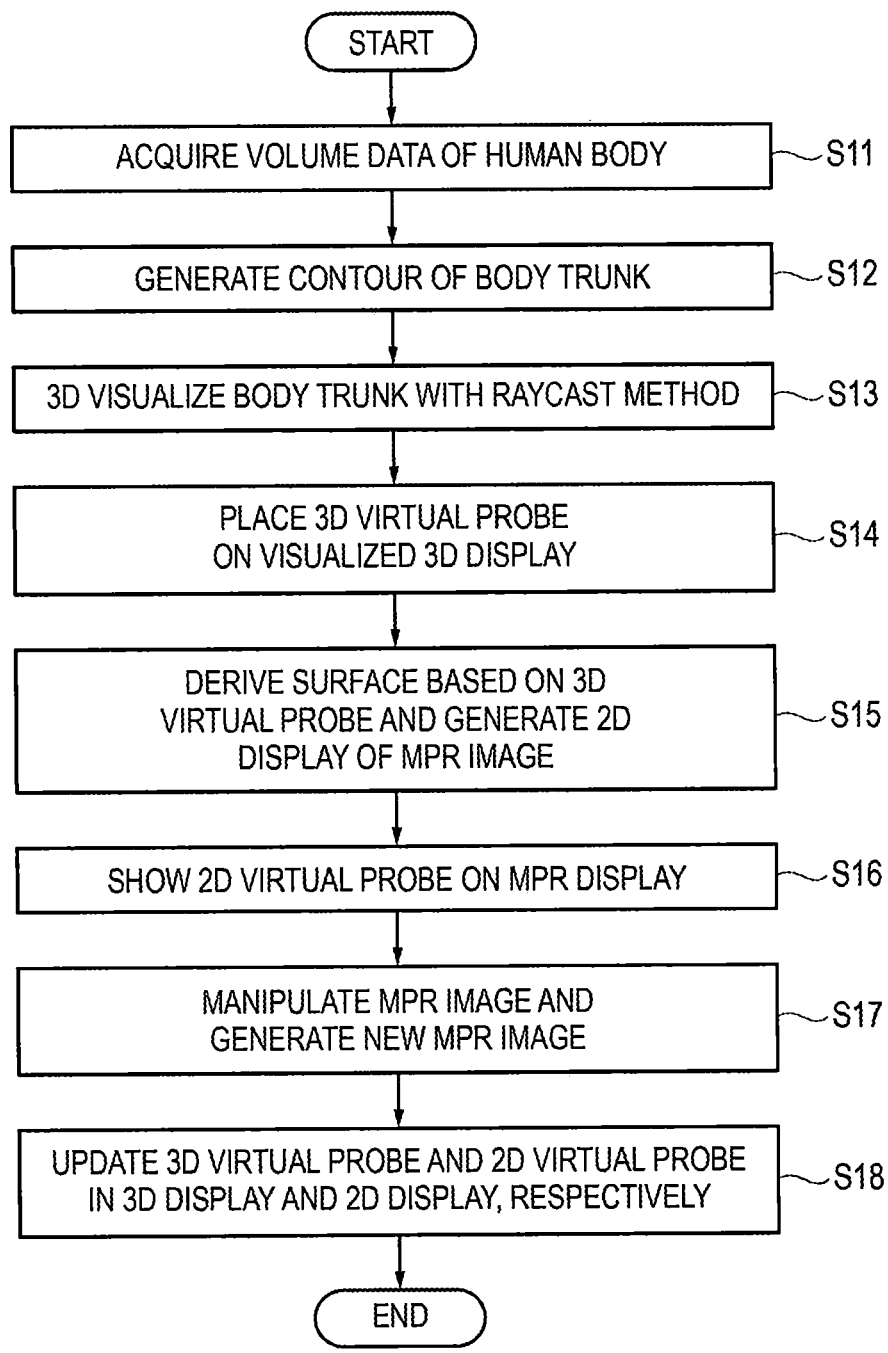
FIG. 8 is a flowchart showing an example of an outline of operations of the medical image processing apparatus.

FIG. 8 is a flowchart showing an example of an outline of operations of the medical image processing apparatus 100.

First, the port 110 acquires volume data of the subject ps from the CT device 200 and the like (S11). The subject ps is, for example, a human body.

The region extraction unit 161 generates contour of a body trunk based on the volume data including the human body (S12). In this case, the region extraction unit 161 may extract volume data in a range surrounded by the contour of the body trunk (that is, volume data of the body trunk) from the volume data including the human body.

The image generation unit 162 visualizes the 3D body trunk of the subject ps with a raycast method (S13). That is, the image generation unit 162 may generate the three-dimensional image G2 showing the body trunk of the subject ps. In this case, the three-dimensional image G2 may be a raycast image. The display control unit 166 may display the generated three-dimensional image G2 on the display 130 (3D display) (S13). The three-dimensional image G2 may be an image other than the raycast image.

The virtual probe processing unit 163 generates the 3D virtual probe pr1. In the initial state, for example, the 3D virtual probe pr1 may be placed so that a virtual light ray is projected onto a central pixel of the generated three-dimensional image G2 and the 3D virtual probe pr1 transmits virtual ultrasound waves to a point which is first touched by the body surface in a normal direction of the body surface pdf. Information in this initial state may be stored in the memory 150. The display control unit 166 places (disposes) the 3D virtual probe pr1 on the visualized 3D display (that is, together with the three-dimensional image G2) (S14).

The image generation unit 162 derives (for example, calculates) a surface based on the coordinates of the virtual probe pr (3D virtual probe pr1). The image generation unit 162 visualizes the derived surface in accordance with an MPR method (S15). The derived surface is the MPR surface SF. That is, the image generation unit 162 may generate 2D display of the MPR image G1 showing the MPR surface SF in the body trunk of the subject ps. The display control unit 166 may display the generated MPR image G1 on the display 130 (2D display) (S15). A two-dimensional image other than the MPR image G1 may be used.

The virtual probe processing unit 163 generates the 2D virtual probe pr2. The 2D virtual probe pr2 uses the coordinates of the 3D virtual probe pr1. The display control unit 166 shows (disposes) and displays the 2D virtual probe pr2 on a two-dimensional display (that is, together with the MPR image G1) (S16).

The operation information acquisition unit 164 acquires various operations on the MPR image G1 through the UI 120. That is, the operation information acquisition unit 164 manipulates the MPR image. The image generation unit 162 generates a new MPR image G1 based on the acquired various operations (based on the manipulated MPR image) (S17). The various operations may include a slice paging operation, a panning operation, a rotation operation, and the like. The virtual probe processing unit 163 generates a new 3D virtual probe pr1 and a new 2D virtual probe pr2 based on the acquired various operations (S17).

The display control unit 166 updates the display of the 3D virtual probe pr1 in the 3D display (S18). That is, the display control unit 166 displays the generated new 3D virtual probe pr1 together with the generated new three-dimensional image G2. The display control unit 166 updates the display of the 2D virtual probe pr2 in the 2D display (S18). That is, the display control unit 166 displays the generated new 2D virtual probe pr2 together with the generated new MPR image G1. In a case where the three-dimensional image G2 itself is not rotated, and the like, the three-dimensional image G2 may not be regenerated, and the original three-dimensional image G2 may be used.

Figure 9:
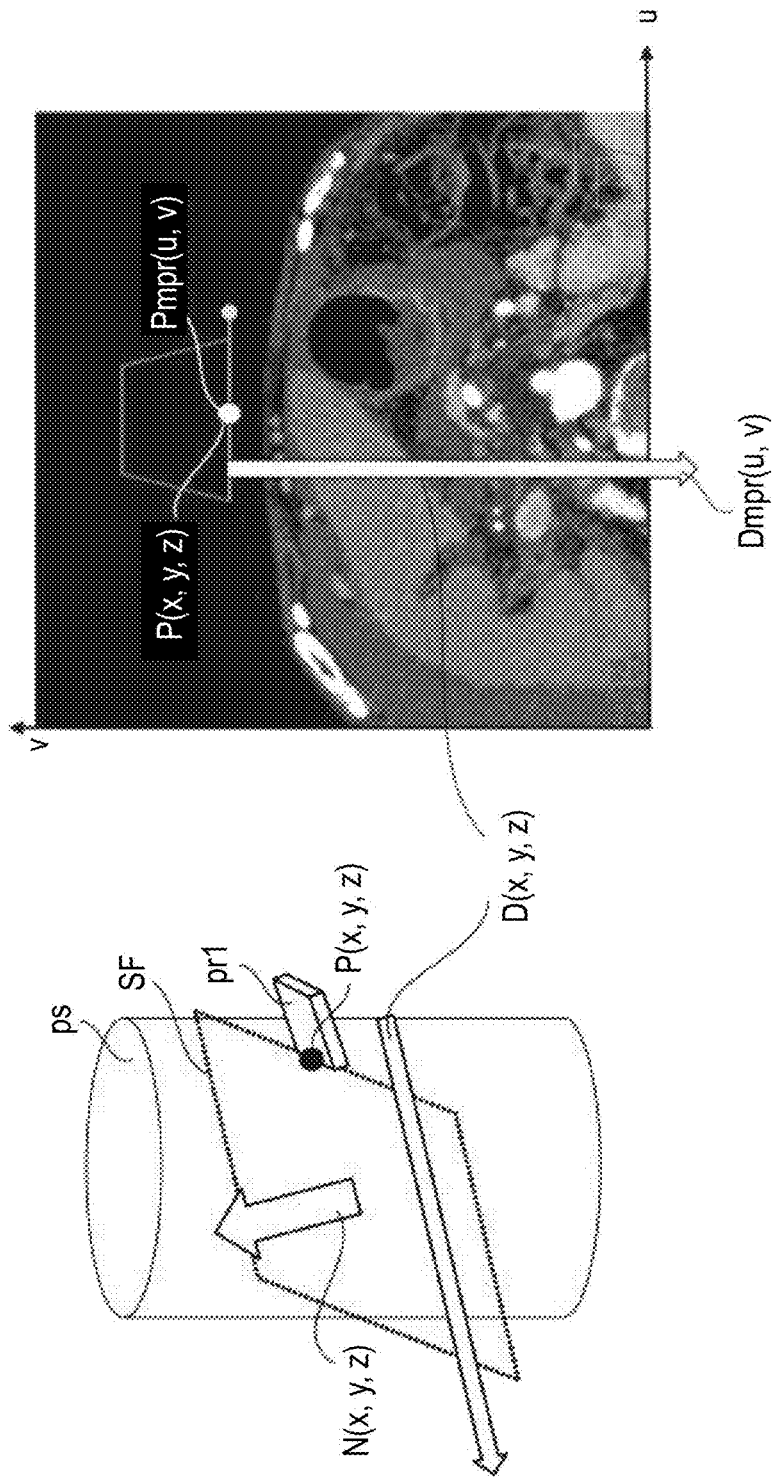
FIG. 9 is a diagram for supplementing description of operations of the medical image processing apparatus according to each operation on an MPR image.

FIG. 9 is a diagram for supplementing description of operations of the medical image processing apparatus 100 according to each operation on the MPR image G1. In FIG. 9, positions and directions in the three-dimensional subject ps and the two-dimensional MPR image G1 are shown. In FIG. 9, a position in a three-dimensional space is indicated by (x, y, and z). In FIG. 9, a position in a two-dimensional plane of the MPR image G1 is indicated by (u, v).

In FIG. 9, a normal (normal line) of the MPR surface SF in the subject ps obliquely viewed is indicated by a normal vector N (x, y, z) (also referred to simply as "N"). Directions of the 3D virtual probe pr1 and the 2D virtual probe pr2 are indicated by a vector D (x, y, z) (also referred to simply as "D") in the three-dimensional space and are indicated by a vector Dmpr (u, v) (also referred to simply as "Dmpr") in the two-dimensional plane of the MPR image G1. Central coordinates of the surface of each of the 3D virtual probe pr1 and the 2D virtual probe pr2 which come into contact with the subject ps are indicated by coordinates P (x, y, z) (also referred to simply as "P") in the three-dimensional space and are indicated by coordinates Pmpr (u, v) (also referred to simply as "Pmpr") in the two-dimensional plane of the MPR image G1.

An initial value of each data may be indicated by attaching "0" to the end of each variable. For example, an initial value of the coordinates P is indicated by P0, an initial value of the coordinates Pmpr is indicated by Pmpr, an initial value of the vector D is indicated by D0, and an initial value of the vector Dmpr is indicated by Dmpr0.

Figure 10:
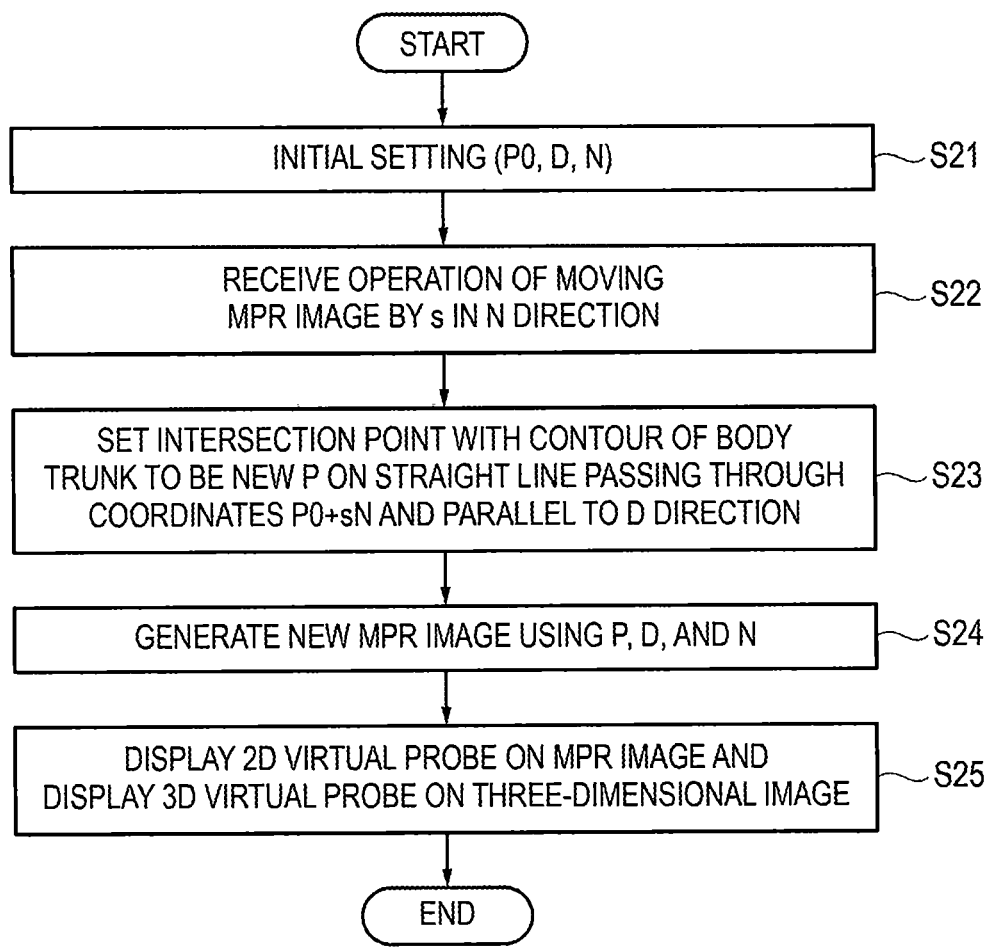
FIG. 10 is a flowchart showing an operation example of the medical image processing apparatus during a slice paging operation on an MPR image.
Figure 15:
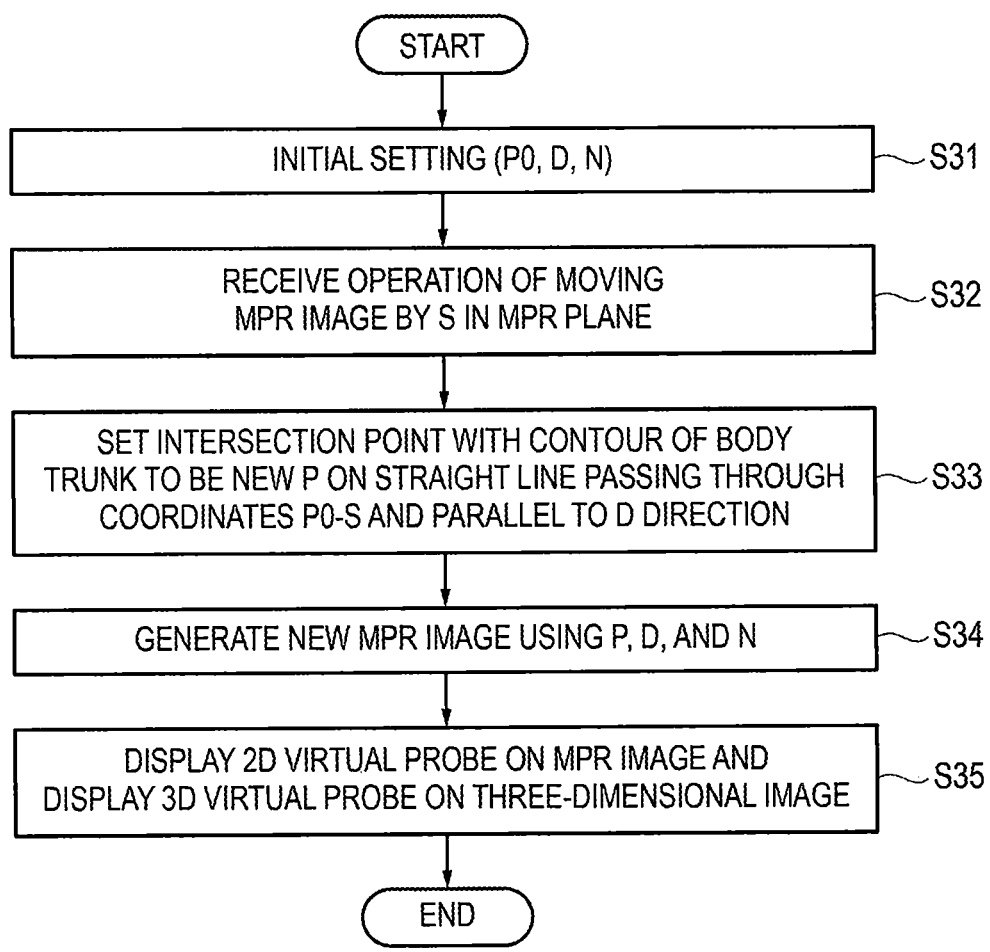
FIG. 15 is a flowchart showing an operation example of the medical image processing apparatus during a panning operation on an MPR image.
Figure 19:
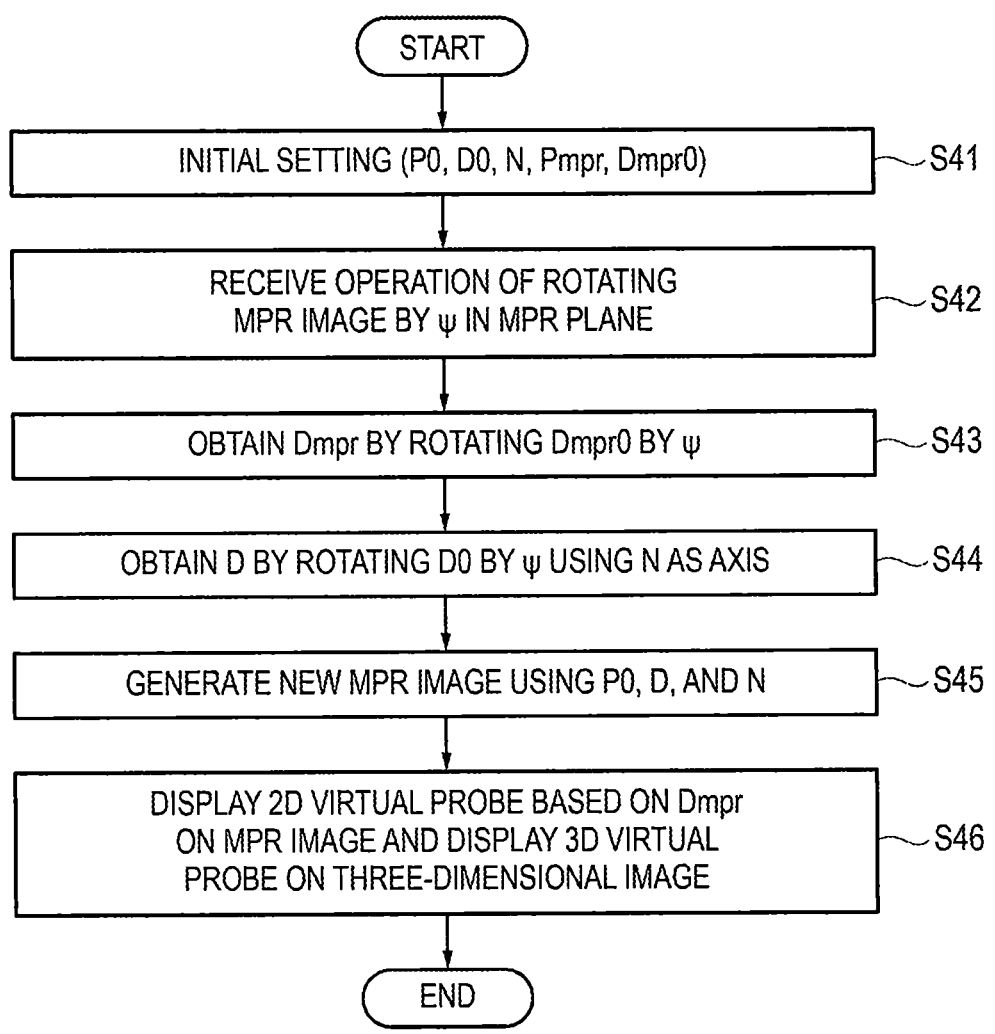
FIG. 19 is a flowchart showing an operation example of the medical image processing apparatus during a rotation operation on an MPR image.

Variables shown in FIG. 9 are used in the description of FIGS. 10, 15 and 19.

FIG. 10 is a flowchart showing an example of operations of the medical image processing apparatus 100 during a slice paging operation on the MPR image G1.

The processing unit 160 performs initial setting of various parameters (S21). That is, the processing unit 160 sets initial values for the central coordinates P0 of the surface of the virtual probe pr which comes into contact with the subject ps, the direction D of the virtual probe pr, and the normal vector N of the MPR surface SF.

The UI 120 receives an operation (slice paging operation) to move the MPR image G1 (MPR surface SF) in an N direction by a distance s (S22). The operation information acquisition unit 164 acquires information of the slice paging operation through the UI 120.

The image generation unit 162 derives (for example, calculates) the central coordinates P of a new surface of the virtual probe pr which comes into contact with the subject ps based on the slice paging operation (S23). In this case, the image generation unit 162 may set an intersection point with the contour (that is, the body surface psf) of the body trunk of the subject ps, which passes through coordinates (also referred to as coordinates P0+sN) moved by s in the N direction from the coordinates P0 and which is positioned on a straight line parallel to the direction D of the virtual probe pr, to be the central coordinates P of the new surface which comes into contact with the subject ps of the virtual probe pr.

In a case where a plurality of central coordinates P described above are derived in S23, the image generation unit 162 may select coordinates close to the coordinates P0+sN among the plurality of central coordinates P. In this case, for example, the medical image processing apparatus 100 can determine so that the central coordinates P continuously move on the body surface psf. That is, the medical image processing apparatus 100 can prevent the virtual probe pr from discontinuously moving on the body surface psf. For example, when volume data is obtained by a CT image using the CT device 200, it is assumed that an arm portion is present together with the body trunk in a transmission direction of virtual ultrasound waves. In this case, the medical image processing apparatus 100 can prevent the central coordinates P from discontinuously moving from the body trunk to the arm portion to perform adjustment so that the central coordinates P continuously move in the body trunk. Accordingly, for example, even when an arm of a patient is included in volume data, the medical image processing apparatus 100 can adjust so that the central coordinates P move continuously in the body trunk.

The image generation unit 162 determines a new MPR surface SF based on the central coordinates P, the direction D of the virtual probe pr, and the normal vector N to generate a new MPR image G1 of the new MPR surface SF (S24).

The virtual probe processing unit 163 generates a new 3D virtual probe pr1 and a 2D virtual probe pr2 based on the central coordinates P, the direction D of the virtual probe pr, and the normal vector N. The display control unit 166 displays the new 3D virtual probe pr1 on the three-dimensional image G2 (S25). The display control unit 166 displays the new 2D virtual probe pr2 on the MPR image G1 (S25).

In a case where a slice paging operation on the MPR image G1 is continued, information of the slice paging operation is continuously acquired by the operation information acquisition unit 164 through the UI 120. In this case, the processing unit 160 may repeat the processes of S22 to S25.

In this manner, in a case where the MPR image G1 is moved in a depth direction (slice paging is performed) through operations during the slice paging operation on the MPR image G1, the medical image processing apparatus 100 moves the virtual probe pr (3D virtual probe pr1) to the position of the body surface in the moved MPR image G1. Accordingly, the medical image processing apparatus 100 can move the virtual probe pr along the body surface without separating the virtual probe pr from the body surface psf even after the movement of the virtual probe. Accordingly, the user can simply obtain an image of the same area as in a case where ultrasound diagnosis is performed by sliding on the body surface psf with the slice paging operation on the MPR image G1 as a starting point.

Figure 11:
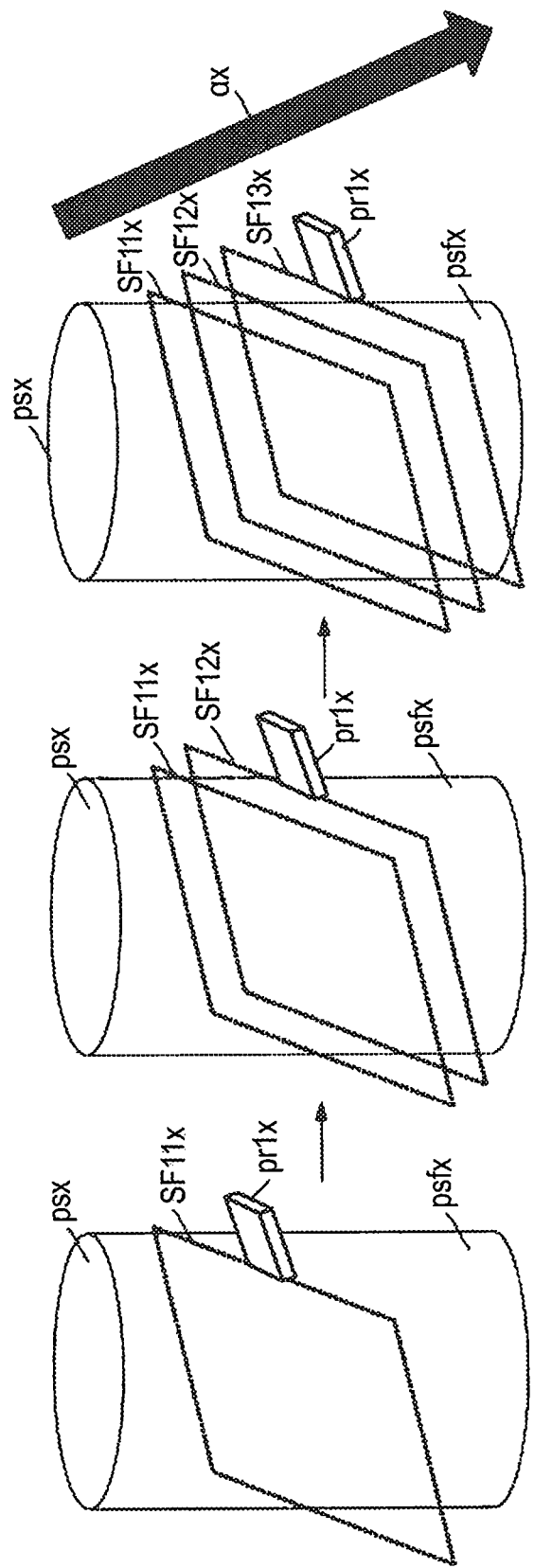
FIG. 11 is a diagram illustrating slice paging according to a slice paging operation in a comparative example.

FIG. 11 is a diagram illustrating slice paging according to a slice paging operation in a comparative example. In the comparative example, in a case where the same target as a target in the description of the present embodiment is described, description will be given by attaching "x" to the end of a reference character in the description of the present embodiment. This is the same as in description of the comparative example related to other operations. Reference characters appearing in the comparative example may not be shown in the drawing.

In FIG. 11, an MPR surface SFx has a predetermined angle with respect to a body surface psfx of a subject psx without being perpendicular thereto. This shows irregularities of the surface of a body. When slice paging is performed on an MPR surface SF11x, the MPR surface SFx is changed to MPR surfaces SF12x, SF13x, . . . parallel to the MPR surface SF11x. Accordingly, a MPR image G1x is changed so as to be moved in parallel in a depth direction or a front direction in the MPR image G1x.

The depth direction and the front direction in the MPR image G1x are directions along an arrow αx. The arrow ax is not parallel to a vertical direction of the body surface psfx in FIG. 11. Accordingly, in a case where a 3D virtual probe pr1x is not designed to move along the body surface psfx, the 3D virtual probe moves along the arrow αx to advance to the inside or outside of the subject psx and separates from the body surface psfx. For this reason, there is a possibility that the MPR image G1x of the user's unintended area in the subject psx may be displayed. Accordingly, it is not appropriate to examine a place to be touched by an ultrasound probe due to the virtual probe pr separating from the body surface.

Figure 12:
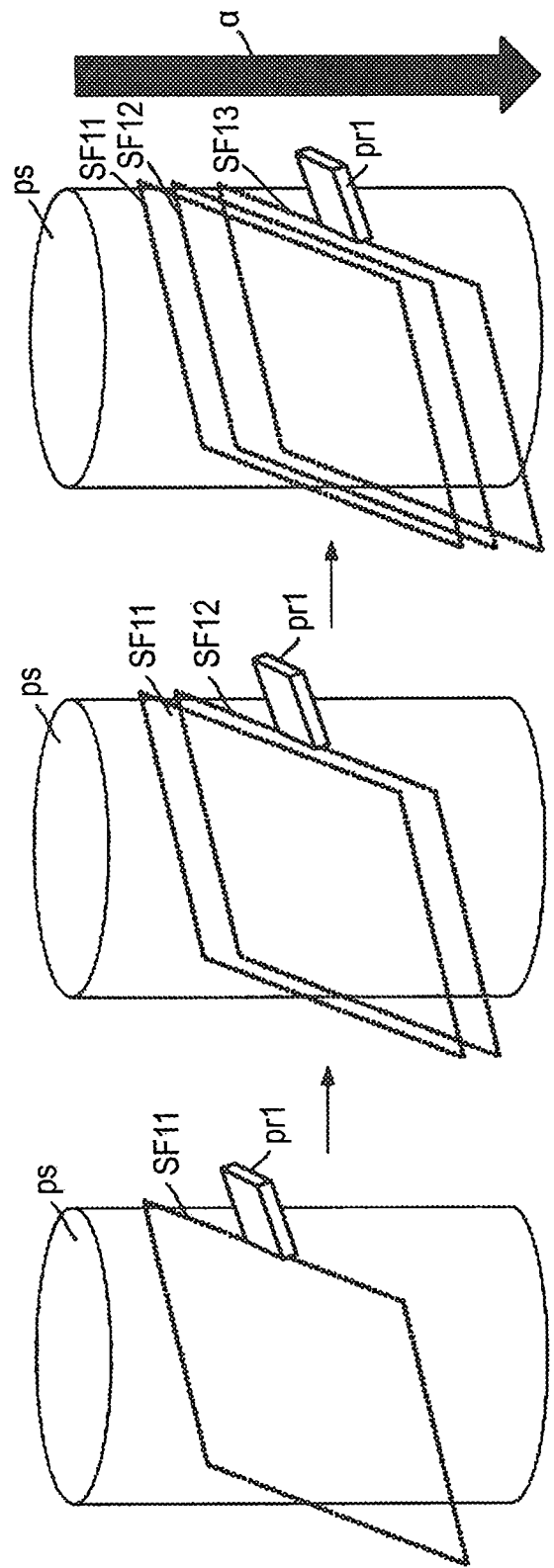
FIG. 12 is a diagram illustrating slice paging according to a slice paging operation in the first embodiment.

FIG. 12 is a diagram illustrating slice paging according to a slice paging operation in the present embodiment. In FIG. 12, the MPR surface SF has a predetermined angle with respect to the body surface psf of the subject ps without being perpendicular thereto. When slice paging is performed on an MPR surface SF11, the MPR surface SF is changed to MPR surfaces SF12, SF13, . . . parallel to the MPR surface SF11.

In a case where slice paging is performed on the MPR image G1, that is, in a case where the MPR image is changed in a depth direction or a front direction in the MPR image G1, the virtual probe processing unit 163 moves the 3D virtual probe pr1 and the 2D virtual probe pr2 to an intersection point (that is, the position of the body surface in the MPR image G1) between the MPR image G1 and the body surface psf which are obtained by performing slice paging. Accordingly, in FIG. 12, the 3D virtual probe pr1 moves along the body surface psf without being separating from the body surface psf. That is, the 3D virtual probe pr1 moves on the body surface psf along the arrow α, and thus the MPR image G1 of the user's intended area in the subject ps is displayed.

The virtual probe processing unit 163 may fix an angle at which the 3D virtual probe pr1 touches the body surface of the subject ps. That is, an angle between the body surface of the subject ps and a transmission direction of virtual ultrasound waves may be fixed. In this manner, the medical image processing apparatus 100 can show a tracing motion while changing the direction of the ultrasound probe in accordance with a curved surface (roundness) of the body surface psf, and thus the medical image processing apparatus approaches the movement of the ultrasound probe depending on an operator. The direction of touching of the 3D virtual probe pr1 may be fixed. This direction may indicate a transmission direction of virtual ultrasound waves. In this manner, the medical image processing apparatus 100 can be maintained in parallel to the MPR surface SF regardless of the curved surface (roundness) of the body surface psf, and thus it is possible to reduce the user's oversight of a disease or the like on the MPR image G1. The direction of the 3D virtual probe pr1 may be maintained so that the MPR surface SF necessarily includes a target (an observation target such as a disease). An angle at which the subject ps is touched by the 3D virtual probe pr1 may correspond to a direction in which virtual ultrasound waves are transmitted and move.

Figure 13:
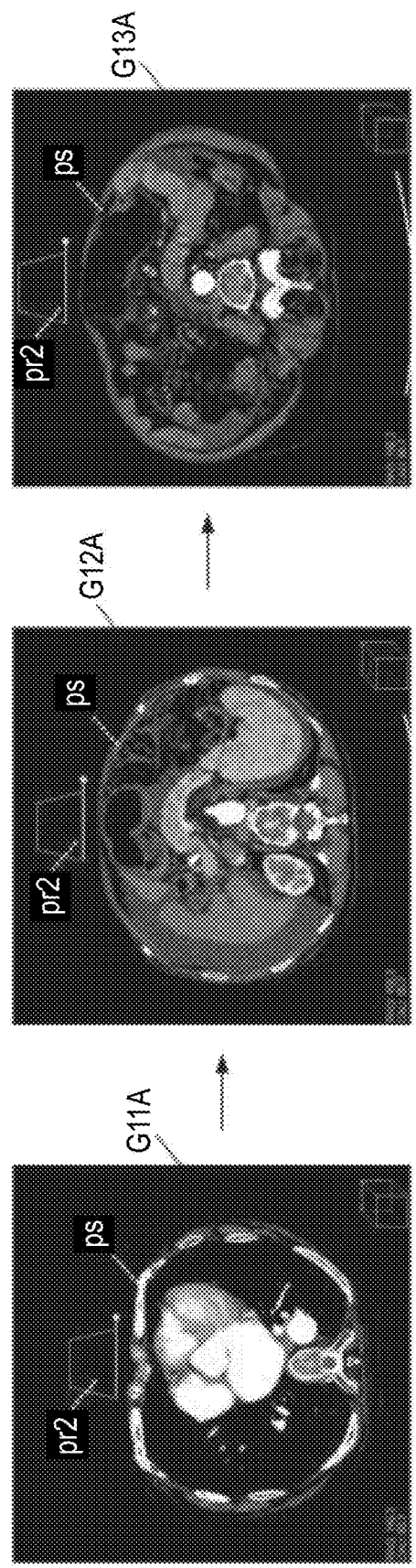
FIG. 13 is a diagram showing an example of transition of an MPR image and a 2D virtual probe according to a slice paging operation on an MPR image in the first embodiment.
Figure 14:
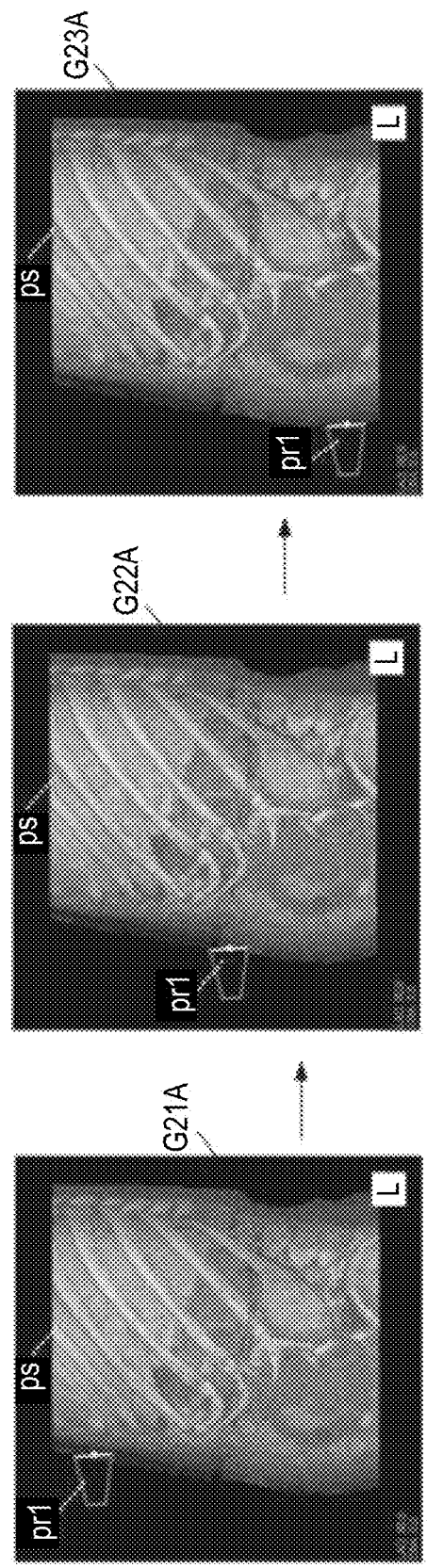
FIG. 14 is a diagram showing an example of transition of a three-dimensional image and a 3D virtual probe according to a slice paging operation on an MPR image in the first embodiment.

FIG. 13 is a diagram showing an example of transition of the MPR image G1A (G11A, G12A, G13A) and the 2D virtual probe pr2 according to a slice paging operation on the MPR image G1A. FIG. 14 is a diagram showing an example of transition of the three-dimensional image G2A (G21A, G22A, G23A) and the 3D virtual probe pr1 according to a slice paging operation on the MPR image G1A.

In FIG. 13, the MPR image G1A is changed in order of the MPR images G11A, G12A, and G13A in accordance with a slice paging operation. In FIG. 14, the three-dimensional image G2A is changed in order of the three-dimensional images G21A, G22A, and G23A in accordance with a slice paging operation. The MPR image G11A and the three-dimensional image G21A indicate the subjects ps at the same timing, the MPR image G12A and the three-dimensional image G22A indicate the subjects ps at the same timing, and the MPR image G13A and the three-dimensional image G23A indicate the subjects ps at the same timing.

In FIG. 13, The 2D virtual probe pr2 does not seem to be enough contact with the body surface psf of the subject ps, but there is a fat layer of the subject ps in a black portion in the vicinity of a white portion having high luminance. That is, the 2D virtual probe pr2 is in contact with the body surface psf of the subject ps in all of the MPR images G11A, G12A, and G13A.

Referring to FIGS. 13 and 14, even when a slice paging operation is performed on the MPR image G1A, the medical image processing apparatus 100 prevents the virtual probe pr (the 3D virtual probe pr1 and the 2D virtual probe pr2) indicating the position and direction of the MPR image G1A of the MPR surface SF from separating from the body surface psf, so that it can be understood that the virtual probe moves on the body surface psf. Accordingly, the medical image processing apparatus 100 can operate an ultrasound image side obtained in the actual ultrasound inspection to update the position and direction of the 3D virtual probe pr1 indicating a position and a direction in a three-dimensional space while following the operation. Accordingly, the user can observe and confirm areas in the entire subject ps from above while performing a fine operation in the MPR image G1A. An example in which the MPR image G1 is moved in parallel in the depth direction has been described as a slice paging operation, but the virtual probe processing unit 163 may move the MPR image in parallel while accompanying panning so that the 2D virtual probe pr2 does not move on the image. The virtual probe processing unit 163 may fix an angle at which the body surface of the subject ps is touched by the 3D virtual probe pr1 and move the MPR image G1 in the depth direction as a slice paging operation.

FIG. 15 is a flowchart showing an example of operations of the medical image processing apparatus 100 during a panning operation for the MPR image G1.

The processing unit 160 performs initial setting of various parameters (S31). That is, the processing unit 160 sets initial values for the central coordinates P0 of the surface of the virtual probe pr which comes into contact with the subject ps, the direction D of the virtual probe pr, and the normal vector N of the MPR surface SF.

The UI 120 receives an operation (panning operation) to move the MPR image G1 by a vector S in a plane of the MPR surface SF (S32). The operation information acquisition unit 164 acquires information of the panning operation through the UI 120.

The image generation unit 162 derives (for example, calculates) the central coordinates P of a new surface of the virtual probe pr which comes into contact with the subject ps based on the panning operation (S33). In this case, the image generation unit 162 may set an intersection point with the contour (that is, the body surface psf) of the body trunk of the subject ps, which passes through coordinates (also referred to as coordinates P0-S) moved by S in a direction opposite to the moving direction of S in S32 from the coordinates P0 and which is positioned on a straight line parallel to the direction D of the virtual probe pr, to be the central coordinates P of the new surface which comes into contact with the subject ps of the virtual probe pr.

In this manner, a display range of the MPR image G1 is moved in a plane of the MPR surface SF by operating the MPR image G1, but the position of the central coordinates P is moved at the same distance as the movement distance of the MPR image G1 in a direction opposite to the moving direction of the MPR image G1. For this reason, it looks as if the position of the 2D virtual probe pr2 is not enough moved on the MPR image G1.

In a case where a plurality of central coordinates P described above are derived in S33, the image generation unit 162 may select coordinates close to the coordinates P0-S among the plurality of central coordinates P. In this case, for example, the medical image processing apparatus 100 can make determination so that the central coordinates P continuously move on the body surface psf. That is, the medical image processing apparatus 100 can prevent the virtual probe pr from discontinuously moving on the body surface psf. For example, when volume data is obtained by a CT image using the CT device 200, it is assumed that an arm portion is present together with the body trunk in a transmission direction of virtual ultrasound waves. In this case, the medical image processing apparatus 100 can prevent the central coordinates P from discontinuously moving from the body trunk to the arm portion to perform adjustment so that the central coordinates P continuously move in the body trunk.

In a case where the central coordinates P are not present in S33, the image generation unit 162 may set a point closest to the coordinates P0-S among points on the contour (that is, the body surface psf) of the body trunk to be the central coordinates P of the new surface which comes into contact with the subject ps of the virtual probe pr. In this case, the medical image processing apparatus 100 can make the 2D virtual probe pr2 follow the body surface psf by moving the position of the 2D virtual probe pr2 so that the 2D virtual probe pr2 does not separate from the body surface psf even when an operation amount of the panning operation is large and the position of the coordinates P0-S is not present on the moved MPR image G1. Although an example in which the direction Dmpr of the 2D virtual probe pr2 is fixed on the MPR image G1 has been described, the virtual probe processing unit 163 may fix an angle at which the body surface of the subject ps is touched by the 3D virtual probe pr1 and rotate the direction Dmpr of the 2D virtual probe pr2.

The image generation unit 162 determines a new MPR surface SF based on the central coordinates P, the direction D of the virtual probe pr, and the normal vector N to generate a new MPR image G1 of the new MPR surface SF (S34).

The virtual probe processing unit 163 generates a new 3D virtual probe pr1 and 2D virtual probe pr2 based on the central coordinates P, the direction D of the virtual probe pr, and the normal vector N. The display control unit 166 displays the new 3D virtual probe pr1 on the three-dimensional image G2 (S35). The display control unit 166 displays the new 2D virtual probe pr2 on the MPR image G1 (S35).

In a case where a panning operation for the MPR image G1 is continued, information of the panning operation is continuously acquired by the operation information acquisition unit 164 through the UI 120. In this case, the processing unit 160 may repeat the processes of S32 to S35.

In this manner, the medical image processing apparatus 100 moves the 3D virtual probe pr1 and the 2D virtual probe pr2 so as to slide the body surface of the subject ps according to an operation during the panning operation for the MPR image G1. In this case, the medical image processing apparatus 100 can make the 3D virtual probe pr1 and the 2D virtual probe pr2 follow the body surface by finely adjusting the position of the central coordinates P. Accordingly, the medical image processing apparatus 100 can move the virtual probe pr along the body surface without separating the virtual probe pr from the body surface psf even after the movement of the virtual probe. Accordingly, the user can easily obtain an image of the same area as in a case where ultrasound diagnosis is performed by sliding the virtual probe on the body surface psf, with the panning operation for the MPR image G1 as a starting point.

Figure 16:
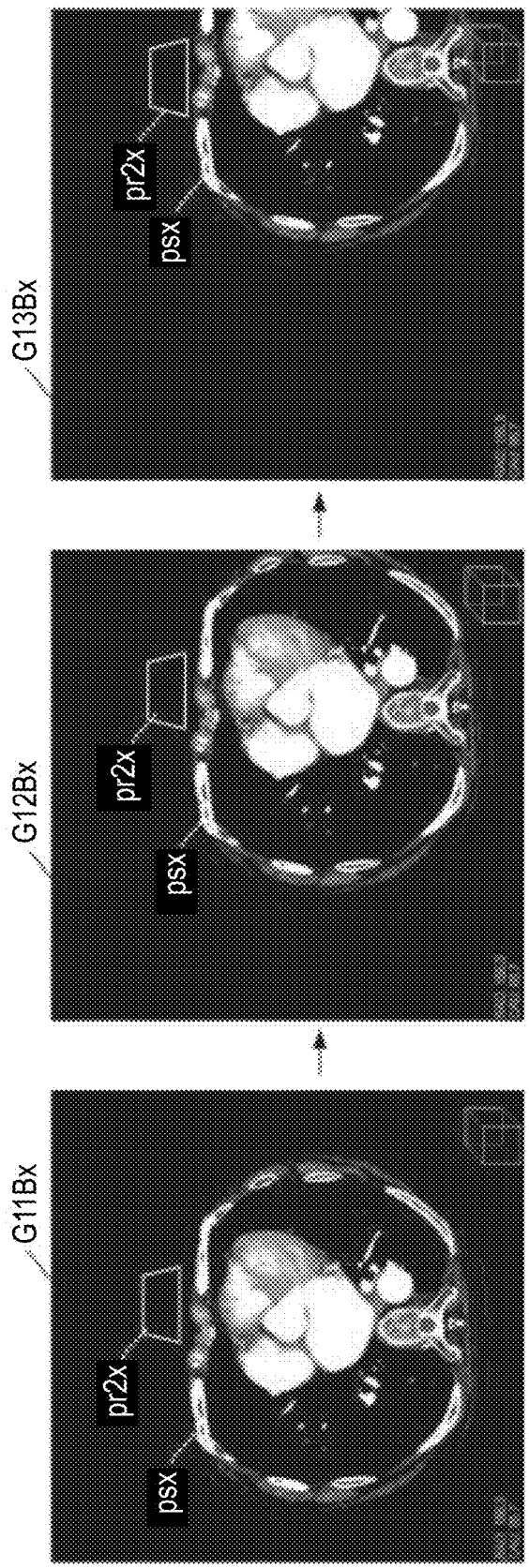
FIG. 16 is a diagram showing transition of an MPR image and a 2D virtual probe according to a panning operation in a comparative example.

FIG. 16 is a diagram showing transition of an MPR image G1Bx (G11Bx, G12Bx, G13Bx) and a 2D virtual probe pr2x according to a panning operation in a comparative example.

In FIG. 16, when the MPR image G1Bx is moved in any direction within an MPR surface SFx according to a panning operation, the position of each point on the MPR image G11Bx displayed on the display 130 is moved. In FIG. 16, the MPR image G1Bx is changed in order of the MPR images G11Bx, G12Bx, G13Bx, . . . . In this case, the 2D virtual probe pr2x is moved according to movement in a plane the MPR surface SFx. That is, a display position of the 2D virtual probe pr2x on the display 130 changes similarly in accordance with a panning operation. For this reason, it is not possible to move the 2D virtual probe pr2x according to a panning operation.

As a comparative example, in a case where the MPR image G1Bx is moved in any direction within the MPR surface SFx according to a panning operation, the 2D virtual probe pr2x may not follow and move at all and the display position of the 2D virtual probe pr2x on the display 130 may not move at all and remains stationary. In this case, the 2D virtual probe pr2x separates from the body surface psf, and thus it is not appropriate to examine a place to be touched by an ultrasound probe.

Figure 17:
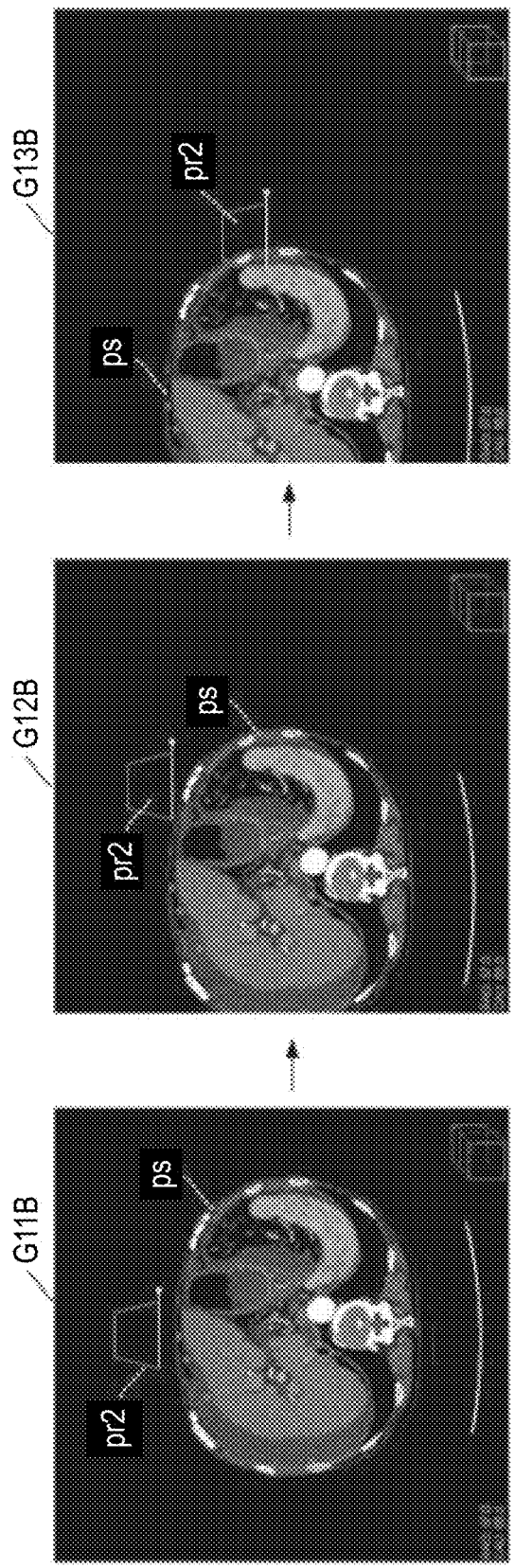
FIG. 17 is a diagram showing an example of transition of an MPR image and a 2D virtual probe according to a panning operation on the MPR image in the first embodiment.
Figure 18:
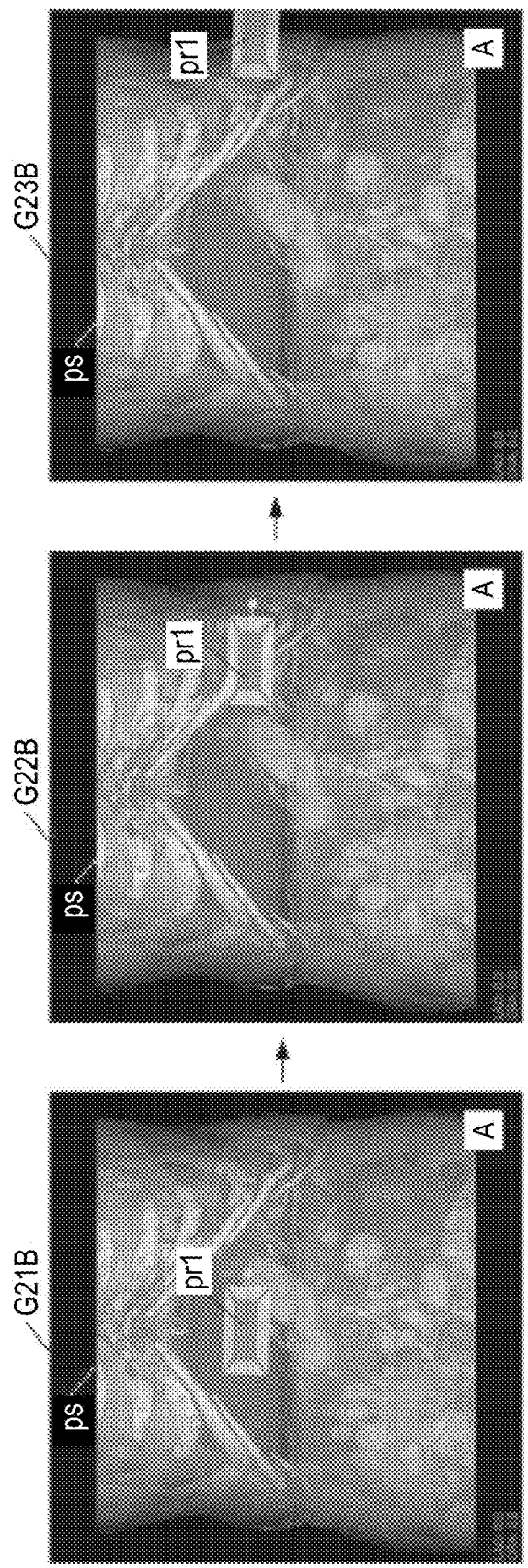
FIG. 18 is a diagram showing an example of transition of a three-dimensional image and a 3D virtual probe according to a panning operation on an MPR image in the first embodiment.

FIG. 17 is a diagram showing an example of transition of an MPR image G1B (G11B, G12B, G13B) and the 2D virtual probe pr2 according to a panning operation for the MPR image G1B in the present embodiment. FIG. 18 is a diagram showing an example of transition of a three-dimensional image G2B (G21B, G22B, G23B) and the 3D virtual probe pr1 according to a panning operation for the MPR image G1B in the present embodiment.

In FIG. 17, when the MPR image G11B is moved in any direction within the MPR surface SF according to a panning operation, the position of each point of the MPR image G11B displayed on the display 130 is moved. In FIG. 17, the MPR image G1B is moved in order of the MPR images G11B, G12B, G13B, . . . . In this case, the 2D virtual probe pr2 is moved at the same movement distance in a direction opposite to a direction of parallel movement of the MPR image G1 within the MPR surface SF. The 2D virtual probe pr2 is moved while maintaining a state where the 2D virtual probe pr2 is in contact with a point on the body surface psf.

In this manner, in FIG. 17, in a case where a panning operation is performed on the MPR image G1B, the display control unit 166 moves and displays the virtual probe pr so as to slide on the body surface psf. In this case, the center of the 2D virtual probe pr2 in a lateral direction is fixed by being aligned with the center of the MPR image G1B in a lateral direction, and the center of the 2D virtual probe pr2 in a vertical direction is moved along the body surface.

Accordingly, the medical image processing apparatus 100 can maintain a contact state between the 2D virtual probe pr2 and the body surface psf while suppressing a change in the display position of the 2D virtual probe pr2 with respect to the display 130 if possible. Therefore, the medical image processing apparatus 100 can use the 2D virtual probe pr2 after operation to examine a place to be touched by an ultrasound probe.

In FIG. 18, when the MPR image G11B is moved in any direction within the MPR surface SF according to a panning operation, the three-dimensional image G21B is not moved, and a display position of the 3D virtual probe pr1 changes. That is, it shows that the position of transmission of virtual ultrasound waves transmitted from the 3D virtual probe pr1 changes in accordance with a panning operation. In FIG. 18, the three-dimensional image G2B transitions in order of the three-dimensional images G21B, G22B, G23B, . . . which correspond to the MPR images G11B, G12B, G13B, . . . , respectively. Accordingly, the user can easily ascertain the position and direction of the MPR image G1B with respect to the three-dimensional image G2B by confirming the position and direction of the 3D virtual probe pr1 together with the three-dimensional image G2B.

In a case where the direction Dmpr of the virtual probe pr faces in a −v direction (see FIG. 9) and the MPR image G1B is moved in parallel in a v direction along the MPR surface SF in accordance with a panning operation, the virtual probe pr may be moved in a +v direction. In a case where the direction Dmpr of the virtual probe pr faces in the −v direction and the MPR image G1B is moved in parallel in a u direction perpendicular to the v direction along the MPR surface SF in accordance with a panning operation, the virtual probe pr is not moved in the u direction and may be moved in the v direction along the body surface psf.

FIG. 19 is a flowchart showing an example of operation of the medical image processing apparatus 100 during a rotation operation for the MPR image G1.

The processing unit 160 performs initial setting of various parameters (S41). That is, the processing unit 160 sets initial values for the central coordinates P0 of the surface of the virtual probe pr which comes into contact with the subject ps, the direction D of the virtual probe pr, the normal vector N of the MPR surface SF, the central coordinates Pmpr in a two-dimensional plane (MPR surface SF) of the surface of the virtual probe pr which comes into contact with the subject ps, and the direction Dmpr0 in a two-dimensional plane (MPR surface SF) of the virtual probe pr.

The UI 120 receives an operation (rotation operation) to rotate the MPR image G1 by an angle Ψ within the MPR surface SF (S42). The operation information acquisition unit 164 acquires information of the rotation operation through the UI 120.

The image generation unit 162 derives (for example, calculates) the direction Dmpr of the virtual probe pr in a two-dimensional plane (MPR surface SF) based on the rotation operation (S43). In this case, the image generation unit 162 may calculate the direction Dmpr of the 2D virtual probe pr2 in a case where the MPR image is rotated by the angle Ψ in a two-dimensional plane from the direction Dmpr0 of the 2D virtual probe pr2 before the rotation operation.

The image generation unit 162 derives (for example, calculates) the direction D of the virtual probe pr in a three-dimensional space based on the rotation operation (S44). In this case, the image generation unit 162 may calculate the direction D of the 3D virtual probe pr1 in a three-dimensional space in a case where the MPR image is rotated by the angle Ψ in a three-dimensional space from the direction D0 of the 3D virtual probe pr1 before the rotation operation by using the normal vector N of the MPR surface SF as an axis.

The image generation unit 162 generates a new MPR image G1 rotated within the MPR surface SF based on the central coordinates P0, the direction D of the virtual probe pr, and the normal vector N (S45).

The virtual probe processing unit 163 generates a new 3D virtual probe pr1 based on the central coordinates P0, the direction D of the virtual probe pr, and the normal vector N. The virtual probe processing unit 163 generates a new 2D virtual probe pr2 based on the central coordinates P0, the direction Dmpr of the virtual probe pr, and the normal vector N. The display control unit 166 displays the new 3D virtual probe pr1 on the three-dimensional image G2 (S46). The display control unit 166 displays the new 2D virtual probe pr2 on the MPR image G1 (S46).

In a case where a rotation operation for the MPR image G1 is continued, information of the rotation operation is continuously acquired by the operation information acquisition unit 164 through the UI 120. In this case, the processing unit 160 may repeat the processes of S42 to S46.

In this manner, the medical image processing apparatus 100 can determine, for example, a contact point between the virtual probe pr and the body surface psf in accordance with an operation during the rotation operation for the MPR image G1 and rotate the MPR image G1 around the contact point on the body surface. That is, the position of the central coordinates P may not change. It is possible to update the display of the virtual probe pr without making the virtual probe pr follow the body surface during the rotation operation.

Figure 20:
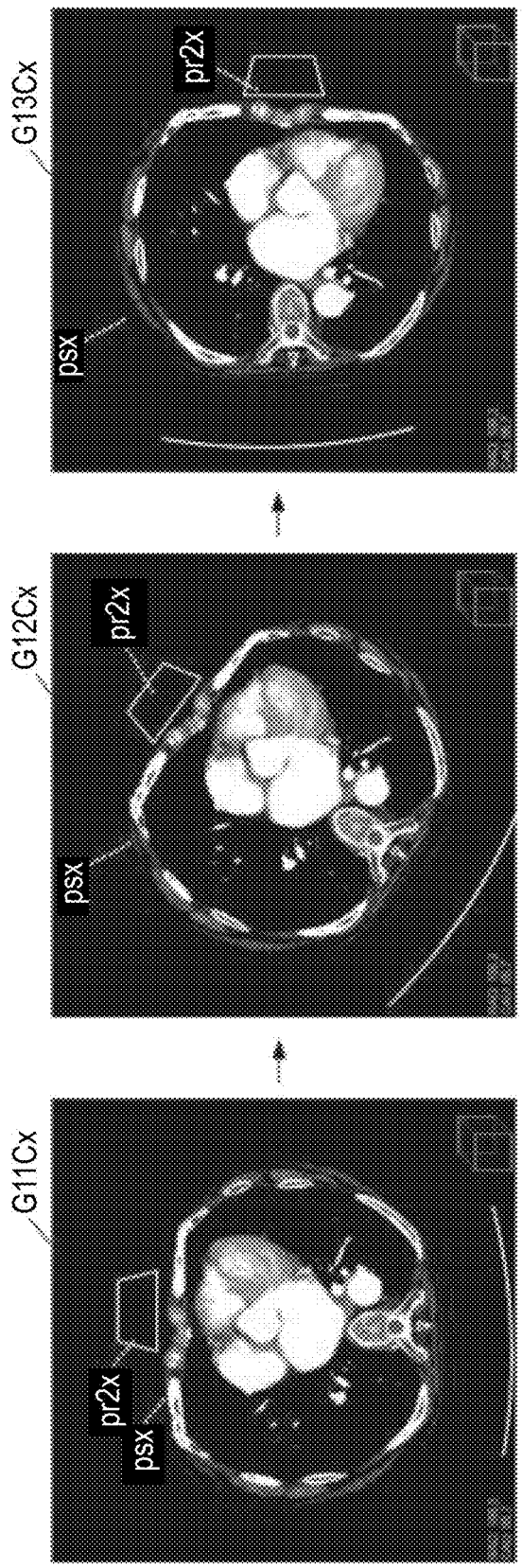
FIG. 20 is a diagram showing transition of an MPR image and a 2D virtual probe according to a rotation operation in a comparative example.

FIG. 20 is a diagram showing transition of an MPR image G1Cx (G11Cx, G12Cx, G13Cx) and a 2D virtual probe pr2x according to a rotation operation in a comparative example.

In FIG. 20, when the MPR image G1Cx is rotated within the MPR surface SFx according to a rotation operation, the position of each point of the MPR image G1Cx displayed on the display 130 is rotated centering on a reference point on the MPR image G1Cx. In FIG. 16, the transition is performed in order of the MPR images G11Cx, G12Cx, G13Cx, . . . . In this case, the 3D virtual probe pr1x on a three-dimensional image G2Cx is rotated in association with the rotation of the body surface psfx in a plane of the MPR surface SFx. That is, the direction of the 2D virtual probe pr2x on the display 130 changes in accordance with the rotation operation, similar to the rotation of the MPR image G1Cx. For this reason, it is not possible to rotate the 2D virtual probe pr2x in accordance with a rotation operation for the MPR image G1.

Figure 21:
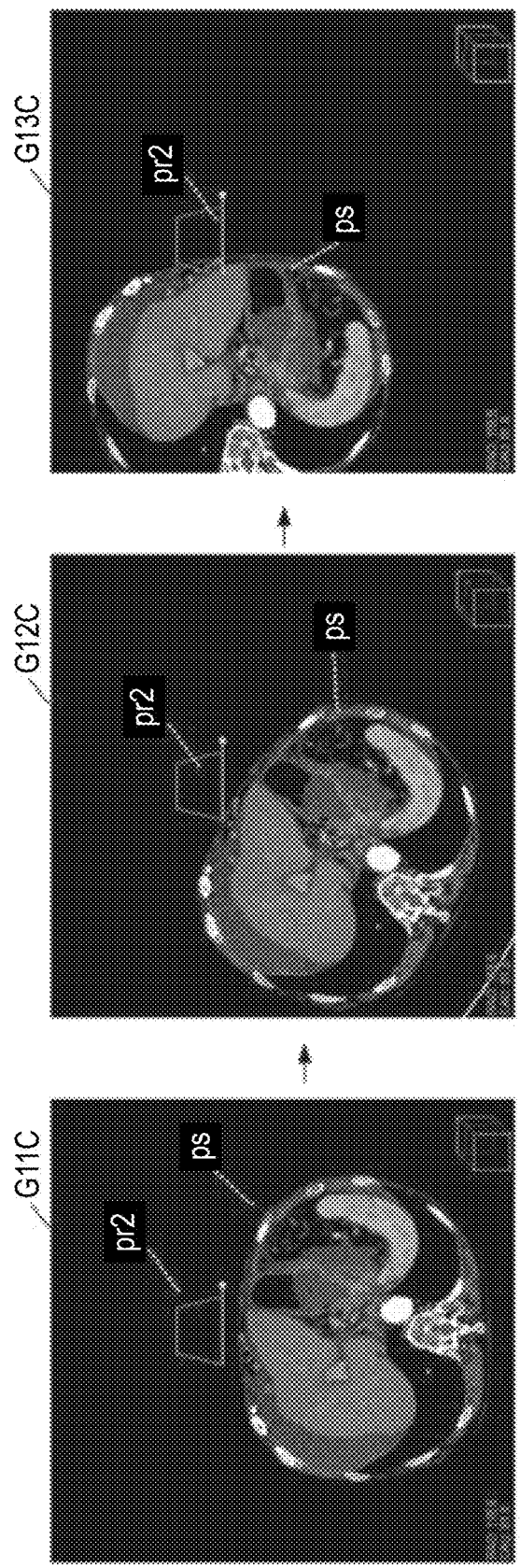
FIG. 21 is a diagram showing an example of transition of an MPR image and a 2D virtual probe according to a rotation operation on the MPR image in the first embodiment.
Figure 22:
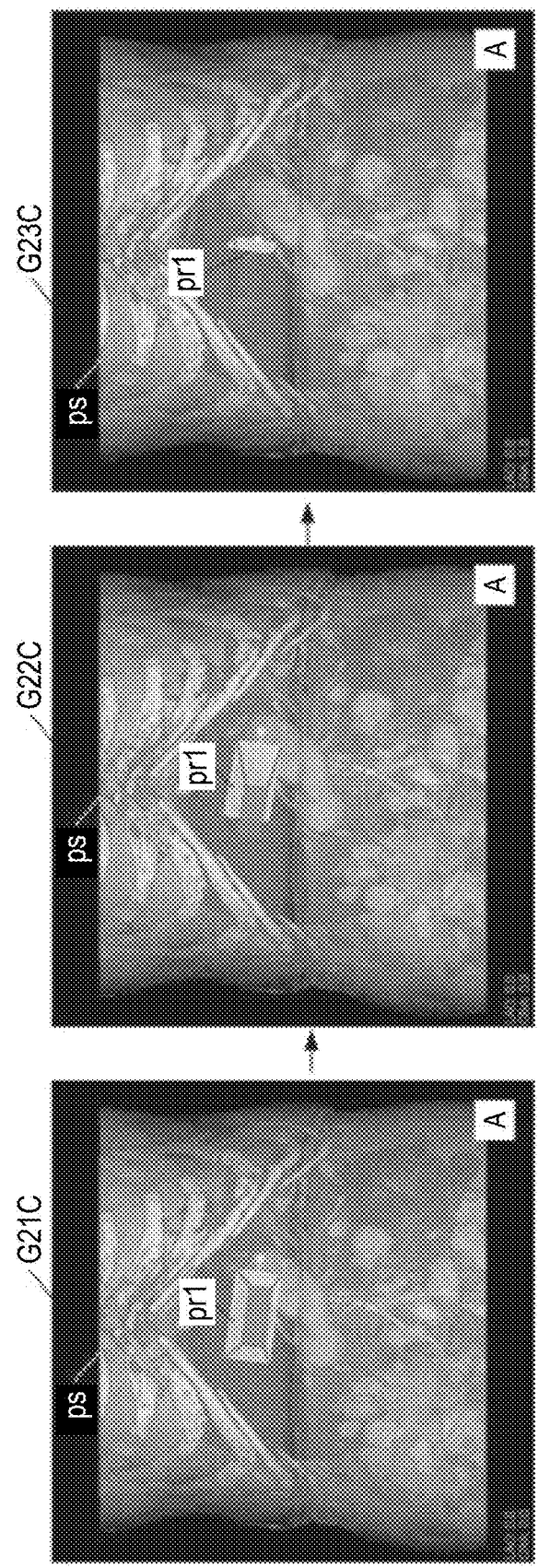
FIG. 22 is a diagram showing an example of transition of a three-dimensional image and a 3D virtual probe according to a rotation operation on an MPR image in the first embodiment.

FIG. 21 is a diagram showing an example of transition of an MPR image G1C (G11C, G12C, G13C) and the 2D virtual probe pr2 according to a rotation operation for the MPR image G1C in the present embodiment. FIG. 22 is a diagram showing an example of transition of a three-dimensional image G2C (G21C, G22C, G23C) and the 3D virtual probe pr1 according to a rotation operation for the MPR image G1C in the present embodiment.

In FIG. 21, when the MPR image G11C is rotated in any direction within the MPR surface SF according to a rotation operation, the position of each point of the MPR image G11B displayed on the display 130 is rotated centering on the position of the 2D virtual probe pr2 (for example, the position of transmission (the central coordinates P of the lower surface ds) of ultrasound waves of the 2D virtual probe pr2). Here, the center of rotation is not limited to one point of the central coordinates P of the lower surface ds, and may be a range in the vicinity of the central coordinates P of the lower surface ds or may have a certain degree of width from the central coordinates P of the lower surface ds. In FIG. 21, the MPR image G1C transitions in order of the MPR images G11C, G12C, G13C, . . . . On the other hand, in FIG. 21, the 2D virtual probe pr2 is not rotated regardless of the rotation of the MPR image G1 within the MPR surface SF. That is, in FIG. 21, a transmission direction of virtual ultrasound waves is a lower direction which is fixed in the 2D virtual probe pr2. Therefore, the 2D virtual probe pr2 is rotated counterclockwise (leftward) with respect to the body surface psf of the subject ps. However, in FIG. 21, it looks as if the 2D virtual probe pr2 is not rotated and the subject ps is relatively rotated clockwise (rightward) with respect to the 2D virtual probe pr2.

The 2D virtual probe pr2 is rotated while maintaining a state where the 2D virtual probe pr2 is in contact with a point on the body surface psf. Accordingly, the medical image processing apparatus 100 can confirm the subject ps which is an observation target from various angles along the MPR surface SF and can maintain a contact state between the body surface psf and the 2D virtual probe pr2.

Therefore, the medical image processing apparatus 100 can improve display accuracy of the position and direction of the 2D virtual probe pr2 after operation and can prevent relative positions and directions between the three-dimensional image G2 and the MPR image G1 after a rotation operation from being deviated.

In FIG. 22, when the MPR image G11C is rotated in any direction within the MPR surface SF according to a rotation operation, the three-dimensional image G21C is not rotated and the display direction of the 3D virtual probe pr1 changes. That is, it is indicated that a transmission direction of virtual ultrasound waves transmitted from the 3D virtual probe pr1 changes in accordance with a rotation operation. In FIG. 21, the three-dimensional image G2C transitions in order of the three-dimensional images G21C, G22C, G23C, . . . which correspond to the MPR images G11C, G12C, G13C, . . . , respectively. Accordingly, the user can easily ascertain the position and direction of the MPR image G1C with respect to the three-dimensional image G2C by confirming the position and direction of the 3D virtual probe pr1 together with the three-dimensional image G2C.

In this manner, according to the medical image processing apparatus 100 of the present embodiment, the user can update the display of a three-dimensional image shown by the MPR image G1 or the virtual probe pr indicating a positional relationship between the MPR image G1 and the three-dimensional image G2 by operating the position and direction of the MPR image G1 through the UI 120. Accordingly, the medical image processing apparatus 100 can indicate which position and direction in the three-dimensional image the position and direction of the MPR image G1 indicate based on the position and direction of the virtual probe pr in accordance with a received operation (for example, a slice paging operation, a panning operation, or a rotation operation). Accordingly, the user can easily ascertain the positional relationship by conforming the direction and position of the virtual probe pr.

Accordingly, for example, the user observes the inside of the subject ps in the MPR image G1 displayed on the display 130 and can observe an area required to be checked in detail from above in the three-dimensional image G2 displayed on the display 130 in a case where the area is present.

The medical image processing apparatus 100 can be used for image processing for performing virtual ultrasound diagnosis. The virtual ultrasound diagnosis may include virtual transesophageal ultrasound diagnosis.

Up to here, although various embodiments have been described with reference to the accompanying drawings, it is needless to say that the present disclosure is not limited to such examples. It would be apparent for those skilled in the art that various modification examples or corrected examples are conceivable within the scope recited in the claims, and it would be understood that these fall within the technical scope of the invention.

In the first embodiment, the region extraction unit 161 may extract a body trunk except for an arm portion of the subject ps. That is, the region extraction unit 161 may execute an algorithm for extracting the body trunk except for the arm portion. Thereby, for example, it is possible to prevent the virtual probe pr from being discontinuously moved from a trunk portion included in the body trunk to the arm portion in accordance with the user's operation for the MPR image G1.

In the first embodiment, an example in which the region extraction unit 161 collectively extracts the entire contour (that is, the body surface psf) of the body trunk of the subject ps has been described, but the disclosure is not limited thereto. In a case where information of an operation for the MPR image G1 is acquired by the operation information acquisition unit 164, the region extraction unit 161 may extract the contour of the body trunk by limiting a range to the contour of the body trunk in the vicinity of the virtual probe pr. The region extraction unit 161 may sequentially extract the contours of the body trunk in the vicinity of the moved virtual probe pr in accordance with an operation for the MPR image G1. Thereby, for example, the extraction of a contour can be omitted with respect to a portion having a contour which is not necessary for the derivation of a contact point between the virtual probe pr and the human body among the contours of the body trunk of the subject ps. Also in this case, the medical image processing apparatus 100 can reduce the amount of arithmetic operation performed by the processing unit 160 while specifying the position and direction of the 3D virtual probe pr1 on the MPR image G1 or the three-dimensional image G2.

In the first embodiment, an example in which the region extraction unit 161 extracts the contour of the body trunk in accordance with region growing has been described, but the contour of the body trunk may be extracted using other methods. For example, the region extraction unit 161 may derive (for example, calculate) coordinates where reflected light used in deriving a raycast image is generated or coordinates where reflected light is accumulated by a threshold value th1 or greater as the contour of the body trunk. Thereby, the medical image processing apparatus 100 can share a portion of arithmetic operation for deriving the contour of the body trunk and arithmetic operation for generating a raycast image and can reduce the amount of arithmetic operation of the processing unit 160.

In the first embodiment, a shape shown in FIG. 4A is exemplified as the shape of the 3D virtual probe pr1 on the three-dimensional image G2, but the disclosure is not limited thereto. For example, the 3D virtual probe pr1 may be indicated by arrows representing the position of transmission of virtual ultrasound waves (transmission starting position) and a transmission direction thereof. The 3D virtual probe pr1 may be indicated by two points representing a transmission starting position of virtual ultrasound waves and a passage position of virtual ultrasound waves. For example, the 3D virtual probe pr1 may be indicated by two points representing one point of a transmission starting position of virtual ultrasound waves and one point within a target. In these cases, it is possible to sufficiently confirm the position and direction of transmission of virtual ultrasound waves and to simplify the 3D virtual probe pr1.

In the first embodiment, a shape shown in FIG. 4B is exemplified as the shape of the 2D virtual probe pr2 on the MPR image G1, but the disclosure is not limited thereto. For example, the 2D virtual probe pr2 may be indicated by arrows representing the position of transmission of virtual ultrasound waves (transmission starting position) in the MPR image G1 and a transmission direction thereof. In a case where a transmission direction (for example, a vertical direction on the image) of ultrasound waves on the MPR image G1 is fixedly determined in advance, the 2D virtual probe pr2 may be indicated by one point representing the position of transmission of virtual ultrasound waves. Accordingly, it is possible to simplify the 2D virtual probe pr2.

The position of transmission of virtual ultrasound waves and a transmission direction thereof are shown indirectly by using coordinates of a center point of the MPR image G1, so that the 2D virtual probe pr2 may be clearly shown on the MPR image G1. The indirect visualization may include showing a line of a puncture on the display 130, showing a fan-shaped frame indicating a virtual ultrasound image on the display 130, and the like.

In this manner, the 2D virtual probe pr2 may be or may not be displayed on the display 130. The display control unit 166 may determine whether to display the 2D virtual probe pr2 or not or may switch between display and non-display. Thereby, the medical image processing apparatus 100 can determine whether to display the 2D virtual probe pr2 or not in accordance with the user's intention.

In the first embodiment, in a case where the display of the three-dimensional image G2 and the 3D virtual probe pr1 is updated in accordance with an operation for the MPR image G1, the virtual probe processing unit 163 may generate the 3D virtual probe pr1 so that an angle between the direction D of the 3D virtual probe pr1 on the three-dimensional image G2 and the direction of a normal line of the body surface psf of the subject ps is maintained. The direction D of the 3D virtual probe pr1 may be parallel to the MPR surface SF. The direction D of the 3D virtual probe pr1 and the direction of the normal line of the body surface psf of the subject ps may be or may not be parallel to each other.

In this case, the virtual probe processing unit 163 may rotate the direction of the 3D virtual probe pr1 (that is, may make the direction variable) in a case where the body trunk of the subject ps is regarded as a cylinder and the 3D virtual probe pr1 is moved in a circumferential direction of the body trunk. The virtual probe processing unit 163 may fix the direction of the 3D virtual probe pr1 in a case where the body trunk of the subject ps is regarded as a cylinder and the 3D virtual probe pr1 is moved in an axial direction of the body trunk. In contrast, the direction of the 3D virtual probe pr1 may be fixed in a case where the 3D virtual probe pr1 is moved in the circumferential direction of the body trunk, and the direction of the 3D virtual probe pr1 may be variable in a case where the 3D virtual probe pr1 is moved in the axial direction of the body trunk.

The virtual probe processing unit 163 may rotate the direction of a normal line of the body surface of the subject ps (that is, may make the direction variable) in a case where the body trunk is regarded as a cylinder and the 3D virtual probe pr1 is moved in the circumferential direction of the body trunk. The virtual probe processing unit 163 may fix the direction of the normal line of the body surface of the subject ps in a case where the body trunk is regarded as a cylinder and the 3D virtual probe pr1 is moved in the axial direction of the body trunk. In contrast, the direction of the normal line of the body surface of the subject ps may be fixed in a case where the 3D virtual probe pr1 is moved in the circumferential direction of the body trunk, and the direction of the normal line of the body surface of the subject ps may be variable in a case where the 3D virtual probe pr1 is moved in the axial direction of the body trunk.

Thereby, the virtual probe processing unit 163 may determine whether to maintain the above-described angle or not. The user can easily recognize the direction of the MPR image G1 with respect to the three-dimensional subject ps without depending on the operation for the MPR image G1 by maintaining the above-described angle. The user can observe the subject ps while variously changing the direction of the MPR image G1 with respect to the three-dimensional subject ps in accordance with an operation for the MPR image G1 by not maintaining the above-described angle.

The first embodiment may be applied to a lumen of the subject ps instead of the body surface of the subject ps. That is, when the MPR image G1 is moved or rotated in accordance with an operation for the MPR image G1, the 3D virtual probe pr1 and the 2D virtual probe pr2 may be moved or rotated along the lumen while being in contact with the lumen. The body surface of the subject ps is not limited to the body trunk and may be a head portion or a body surface of a limb. The body surface may be the surface of an organ instead of the body surface of the subject ps. The body trunk of the subject ps may be a portion ranging from an abdomen to a thoracic neck.

In the first embodiment, the image generation unit 162 may visualize using any method such as a raycast method, a MW method limited to a body trunk region, RaySUM limited to a body trunk region, or a surface rendering method including the surface of a body trunk. There may be no limitation to the above-mentioned body trunk region. While the 3D virtual probe pr1 is moved along the body surface, the image generation unit 162 may visualize only an affected area or an organ in the vicinity of the affected area.

In the first embodiment, the image generation unit 162 may visualize using any method such as a so-called thick MPR image, a thick MPR image for performing SUM within a thickness range, or a thick MIP image for performing SUM within a thickness range as an MPR image. The image generation unit 162 may visualize using a so-called pseudo ultrasound image subjected to processing such as simulating a reflected wave from volume data or adding distortion of an edge portion as an MPR image.

In the first embodiment, volume data as an obtained CT image is transmitted from the CT scanner 200 to the medical image processing apparatus 100. Alternatively, volume data may be transmitted to a server or the like on a network and stored in the server or the like so as to be temporarily accumulated. In this case, the port 110 of the medical image processing apparatus 100 may acquire volume data from the server or the like when necessary through a wired circuit or a wireless circuit or may acquire volume data through any storage medium (not shown).

In the first embodiment, volume data as an obtained CT image is transmitted from the CT scanner 200 to the medical image processing apparatus 100 through the port 110. It is assumed that this also includes a case where the CT scanner 200 and the medical image processing apparatus 100 are substantially combined as one product. In addition, this also includes a case where the medical image processing apparatus 100 is treated as a console of the CT scanner 200.

In the first embodiment, an image is obtained by the CT scanner 200 to generate volume data including information regarding the inside of an internal organism. However, an image may be obtained by any of other devices to generate volume data. Other devices include a magnetic resonance imaging (MM) apparatus, a positron emission tomography (PET) device, a blood vessel angiographic device (angiography device), or other modality devices. In addition, the PET device may be used in combination with other modality devices.

In the first embodiment, a human body is described as a subject, but an animal body may also be used.

In the present disclosure, a program for realizing functions of the medical image processing apparatus of the first embodiment is supplied to the medical image processing apparatus through a network or various storage mediums, and the present disclosure is also applicable to a program read out and executed by a computer within the medical image processing apparatus.

As described above, in the medical image processing apparatus 100 of the above-described embodiment, an acquisition unit (for example, the port 110) acquires volume data of the subject ps. The processing unit 160 displays the three-dimensional image G2 by rendering volume data, on a display unit (for example, the display 130). The processing unit 160 displays a first object (for example, the 3D virtual probe pr1) showing (i) a point (for example, the central coordinates P) on the body surface of the subject ps (for example, the body surface psf) and (ii) the direction with respect to volume data (for example, the direction D of the virtual probe pr) on the three-dimensional image G2, on the display unit. The processing unit 160 displays a two-dimensional image (for example, the MPR image G1) of a surface on the display unit. The surface (for example, the MPR surface SF) includes the point on the body surface and is defined based on the direction, in volume data. The processing unit 160 acquires information of a first operation to change the display of a two-dimensional image. The processing unit 160 moves a point on the body surface along the body surface of the subject ps to update the display of the first object and the two-dimensional image based on the above-described first operation.

According to the present disclosure, the user observes the subject ps using a two-dimensional image, for example, at the time of diagnosis and easily understands an accurate position of disease or the like in the subject ps. The user can observe the entire subject ps from above by using the three-dimensional image G2. In this case, the user can ascertain to which position and which direction the two-dimensional image corresponds in the three-dimensional image G2.

The medical image processing apparatus 100 can maintain a state where the subject ps is easily observed by making the position of the 3D virtual probe pr1 on the three-dimensional image G2 follow the body surface of the subject ps. Accordingly, the user convenience is improved.

In a movement operation on the two-dimensional image in a conventional way, a two-dimensional plane is considered, and the surface of the three-dimensional image is not usually considered. On the other hand, the medical image processing apparatus 100 can recognize a surface (the body surface psf) in the subject ps by making the 3D virtual probe pr1 follow the surface on the three-dimensional image G2 in accordance with the operation in the two-dimensional image. The user performs the operation on the two-dimensional image instead of the three-dimensional image G2, and thus the user easily recognizes a direction related to movement and performs a fine operation.

In a case where the user operates the two-dimensional image to update the display thereof, it is easy to ascertain to which position and which direction the updated two-dimensional image corresponds in the three-dimensional image G2.

The above-described first operation may include slice paging of the surface on which the two-dimensional image is shown (for example, the MPR surface SF).

Even when the slice paging operation is performed on the two-dimensional image through an operation unit (for example, the UI 120), the medical image processing apparatus 100 can ascertain to which position and which direction the operated two-dimensional image corresponds in the three-dimensional image.

The medical image processing apparatus 100 can easily move the position of the virtual probe pr1 by the slice paging operation on the two-dimensional image through the operation unit (for example, the UI 120).

The above-described first operation may include moving a display range of the two-dimensional image in parallel on the surface (for example, the MPR surface SF).

Even when a panning operation is performed on the two-dimensional image through the operation unit (for example, the UI 120), the medical image processing apparatus 100 can ascertain to which position and which direction the operated two-dimensional image corresponds in the three-dimensional image.

The medical image processing apparatus 100 can easily move the position of the virtual probe pr1 by performing the panning operation on the two-dimensional image through the operation unit (for example, the UI 120).

The processing unit 160 may acquire information of a second operation to rotate the two-dimensional image on the surface (for example, the MPR surface SF), in addition to the first operation. The processing unit 160 may fix the point on the body surface to update a first object on the three-dimensional image and the two-dimensional image based on the second operation.

Even when the rotation operation is performed on the two-dimensional image through the operation unit (for example, the UI 120), the medical image processing apparatus 100 can ascertain to which position and which direction the operated two-dimensional image corresponds in the three-dimensional image. The medical image processing apparatus 100 may fix the point on the body surface and rotate the two-dimensional image, so that the user can observe the same two-dimensional image from any direction, which facilitates observation.

The medical image processing apparatus 100 can easily move the direction of the virtual probe pr1 by the rotation operation on the two-dimensional image through the operation unit (for example, the UI 120).

The processing unit 160 may extract volume data of the body trunk from volume data of the subject ps to generate the three-dimensional image and the two-dimensional image of the volume data of the body trunk.

The medical image processing apparatus 100 can suppress the generation of a plurality of intersection points between the surface on which the two-dimensional image is rendered (for example, the MPR surface SF) and the body surface of the subject ps. Accordingly, it is possible to suppress discontinuous movement of the first object on the three-dimensional image and a great change in an area of the subject ps shown by the two-dimensional image in accordance with an operation for the two-dimensional image. Accordingly, the user easily observes the subject ps while performing the operation to the two-dimensional image.

The processing unit 160 may update the display of the first object and the two-dimensional image by maintaining an angle between the direction of the vector and the direction of the normal line of the body surface based on the above-described operation.

The user easily recognize the direction of the MPR image G1 with respect to the three-dimensional subject ps without depending on the operation for the MPR image G1 by the medical image processing apparatus 100 maintaining the above-described angle.

The user easily observes the subject by performing a motion close to an operation of tracing the body surface of a patient using an ultrasound probe by the medical image processing apparatus 100 maintaining the above-described angle.

The processing unit 160 may update the display of the first object and the two-dimensional image by maintaining the direction based on the above-described operation.

The user easily recognizes the direction of the MPR image G1 for the three-dimensional subject ps without depending on an operation for the MPR image G1 by the medical image processing apparatus 100 maintaining the direction.

The user easily observes the subject by performing a motion close to an operation of tracing the body surface of a patient using an ultrasound probe by the medical image processing apparatus 100 maintaining the direction.

The processing unit 160 may display a second object (for example, the 2D virtual probe pr2) showing (iii) a point on the body surface of the subject ps and (iv) the direction in the two-dimensional image on a display unit.

The medical image processing apparatus 100 can display the second object indicating a position and a direction similar to the first object, together with the two-dimensional image. Accordingly, the user can confirm information of the position and direction of the two-dimensional image in the three-dimensional image on the two-dimensional image. Therefore, the user convenience is improved.

The direction may indicate a transmission direction of virtual ultrasound waves. The above-described surface may indicate the surface along a passage through which virtual ultrasound waves pass.

The medical image processing apparatus 100 can set the direction and the surface related to virtual ultrasound waves. Accordingly, the user easily ascertains to which position and which direction the two-dimensional image corresponds in the three-dimensional image G2, in a case where diagnosis using the virtual ultrasound image is performed.

The present disclosure is useful for a medical image processing apparatus, a medical image processing method, and a medical image processing system which are capable of ascertaining to which position and which direction a changed two-dimensional image corresponds in a three-dimensional image in a case where a user operates the two-dimensional image to update display thereof

What is claimed is:

1. A medical image processing apparatus comprising:
   an acquisition unit that is configured to acquire volume data of a subject; and
   a processing unit that is configured to:
      display a three-dimensional image by rendering the acquired volume data, on a display unit;
      display a first user interface (UI) object showing (i) a point on a body surface of the subject and (ii) a direction with respect to the volume data, in the three-dimensional image on the display unit;
      display a two-dimensional image of a cross-section on the display unit, wherein the cross-section includes the point on the body surface and is defined based on the direction, in the volume data;
      acquire information of a first operation to change display of the two-dimensional image; and
      move the point on the body surface along the body surface of the subject based on the first operation to update display of the first UI object and the two-dimensional image.

2. The medical image processing apparatus according to claim 1, wherein the first operation includes slice paging of the surface on which the two-dimensional image is shown.

3. The medical image processing apparatus according to claim 1, wherein the first operation includes moving a display range of the two-dimensional image in parallel on the surface.

4. The medical image processing apparatus according to claim 1, wherein the processing unit is configured to:
   acquire information of a second operation to rotate around the point on the body surface the two-dimensional image on the surface, in addition to the first operation; and
   update the display of the first UI object on the three-dimensional image and the two-dimensional image based on the second operation.

5. The medical image processing apparatus according to claim 1, wherein the processing unit is configured to:
   extract body trunk from the volume data of the subject, and
   generate the three-dimensional image and the two-dimensional image of the body trunk.

6. The medical image processing apparatus according to claim 1, wherein the processing unit is configured to maintain an angle between the direction and a direction of a normal line with respect to the body surface to update the display of the first UI object and the two-dimensional image based on the first operation.

7. The medical image processing apparatus according to claim 1, wherein the processing unit is configured to maintain the direction to update the display of the first UI object and the two-dimensional image based on the first operation.

8. The medical image processing apparatus according to claim 1, wherein the processing unit is configured to display a second UI object showing (iii) the point on the body surface of the subject and (iv) the direction, in the two-dimensional image on the display unit.

9. The medical image processing apparatus according to claim 1, wherein
   the direction indicates a transmission direction of virtual ultrasound waves, and
   the surface indicates a surface along a passage through which the virtual ultrasound waves pass.

10. A medical image processing method in a medical image processing apparatus, the method comprising:
   acquiring volume data of a subject;
   displaying a three-dimensional image by rendering the acquired volume data;
   displaying a first user interface (UI) object showing (i) a point on a body surface of the subject and (ii) a direction with respect to the volume data in the three-dimensional image;
   displaying a two-dimensional image of a cross-section, wherein the cross-section includes the point on the body surface and is defined based on the direction, in the volume data;
   acquiring information of an operation to change display of the two-dimensional image; and
   moving the point on the body surface along the body surface of the subject based on the operation to update display of the first UI object and the two-dimensional image.

11. A medical image processing system causing a medical image processing apparatus to execute the medical image processing operations comprising:

acquiring volume data of a subject;

displaying a three-dimensional image by rendering the acquired volume data;

displaying a first user interface (UI) object showing (i) a point on a body surface of the subject and (ii) a direction with respect to the volume data in the three-dimensional image;

displaying a two-dimensional image of a cross-section, wherein the cross-section includes the point on the body surface and is defined based on the direction, in the volume data;

acquiring information of an operation to change display of the two-dimensional image; and moving the point on the body surface along the body surface of the subject based on the operation to update display of the first UI object and the two-dimensional image.

\* \* \* \* \*